(12) United States Patent
Thompson et al.

(10) Patent No.: US 9,308,215 B2
(45) Date of Patent: Apr. 12, 2016

(54) AVERMECTINS AND MILBEMYCINS AS ANTI-MYCOBACTERIAL AGENTS

(71) Applicants: Charles J. Thompson, Vancouver (CA); Santiago Ramon-Garcia, Vancouver (CA); Leah Elizabeth Lim, Seattle, WA (US)

(72) Inventors: Charles J. Thompson, Vancouver (CA); Santiago Ramon-Garcia, Vancouver (CA); Leah Elizabeth Lim, Seattle, WA (US)

(73) Assignees: Charles J. Thompson, Vancouver, BC (CA); Santiago Ramon-Garcia, Madrid (ES); Leah Elizabeth Lim, Vancouver, BC (CA)

( * ) Notice: Subject to any disclaimer, the term of this patent is extended or adjusted under 35 U.S.C. 154(b) by 0 days.

(21) Appl. No.: 14/254,747

(22) Filed: Apr. 16, 2014

(65) Prior Publication Data

US 2014/0315842 A1    Oct. 23, 2014

Related U.S. Application Data

(60) Provisional application No. 61/812,979, filed on Apr. 17, 2013.

(51) Int. Cl.
*A61K 31/35*    (2006.01)
*A61K 31/7048*    (2006.01)

(52) U.S. Cl.
CPC ............. *A61K 31/7048* (2013.01); *A61K 31/35* (2013.01)

(58) Field of Classification Search
CPC ........................... A61K 31/7048; A61K 31/35
See application file for complete search history.

(56) References Cited

PUBLICATIONS

World Health Organization, "Global Tuberculosis Report" Geneva, Switzerland, 2012, 100 pages.
Jassal and Bishai "Extensively drug-resistant tuberculosis" Lancet. Infect. Dis., 2009, 9:19-30.
Rowland "Totally drug-resistant TB emerges in India" Nature, 2012.
Chiang et al. "Drug-resistant tuberculosis: past, present, future" Respirology, 2010, 15:413-432.
Lim et al. "Anthelmintic Avermecins Kill *Mycobacterium tuberculosis*, inculsing multidrug v-resistant clinical strains" Antimicrob. Agents. Chemother., 2013, 57:1040-1046.
Ameen and Drancourt, "Comment on: Measurements of the in vitro anti-mycobacterial activity of ivermectin are method-dependent", The Journal of antimicrobial chemotherapy, 2014, 69(6): 1724-1725.
Ameen and Drancourt, "Ivermectin lacks antituberculous activity" *J Antimicrob Chemother* 2013, 68:1936-7.
Bryant, J. M. et al., "Whole-genome sequencing to identify transmission of *Mycobacterium* abscessus between patients with cystic fibrosis: a retrospective cohort study", Lancet, 2013, 381:1551-1560.
Dartois V., "The path of anti-tuberculosis drugs: from blood to lesions to mycobacterial cells", Nature reviews Microbiology, 2014, 12:159-67.
Canga et. al., "The pharmacokinetics and interactions of ivermectin in humans—a mini-review" The AAPS journal, 2008, 10(1):42-46.
Griffith, DE. et al., "An official ATS/IDSA statement: diagnosis, treatment, and prevention of nontuberculous mycobacterial diseases", Am J Respir Crit Care Med., 2007, 175(4):367-416.
Griffith, D. E. et al., "Clinical features of pulmonary disease caused by rapidly growing mycobacteria", Am Rev Respir Dis., 1993, 147:1271-1278.
Guzzo CA et al., "Safety, tolerability, and pharmacokinetics of escalating high doses of ivermectin in healthy adult subjects", Journal of clinical pharmacology, 2002; 42:1122-1133.
Jayaram R, et al., "Pharmacokinetics-pharmacodynamics of rifampin in an aerosol infection model of tuberculosis", Antimicrob. Agents Chemother., 2003, 47:2118-2124.
Koul, A., et al., "The challenge of new drug discovery for tuberculosis", Nature, 2011, 469:483-490.
Lim et al., "Anthelmintic Avermectins Kill *Mycobacterium tuberculosis*, Including Multidrug-Resistant Clinical Strains", Antimicrob. Agents Chemother, 2013, 57:1040-1046.
Logie, et al. "Challenges faced by multidisplinary new investigators on addressing grand challenges in global health", Globalization and Health Health, 2014, 10(27):1-8.
McKellar, Q. A., and C. Gokbulut, "Pharmacokinetic features of the antiparasitic macrocyclic lactones", Curr Pharm Biotechnol, 2012, 13:888-911.
Morris, Rowan P., et al. "Ancestral antibiotic resistance in *Mycobacterium tuberculosis*", Proc Natl Acad Sci, 2005, 102:12200-12205.
Nagai, K., "Synthesis and biological evaluation of novel 4"-alkoxy avermectin derivatives", Bioorg Med Chem Lett, 2004, 14:4135-4139.
Olivier, KN. et al., "The natural history of nontuberculous mycobacteria in patients with cystic fibrosis" Paediatric respiratory reviews, 2004, 5(Suppl A):S213-216.
Omura, S., and A. Crump. "The life and times of ivermectin—a success story" Nat Rev Microbiol, 2004, 2:984-989.
Parrish, S. C., "Nontuberculous mycobacterial pulmonary infections in Non-HIV patients", Postgraduate medicine, 2008, 120:78-86.
Radhakrishnan, DK. et al., "Non-tuberculous mycobacteria in children with cystic fibrosis: isolation, prevalence, and predictors", Pediatric pulmonology, 2009, 44:1100-1106.
Rallis and Koumantaki-Mathioudaki, "Treatment of *Mycobacterium marinum* cutaneous infections", Informa Healthcare, Expert Opin. Pharmacother, 2007, 8(17):2965-2978.
Ramon-Garcia S. et al., "Synergistic drug combinations for tuberculosis therapy identified by a novel high-throughput screen", Antimicrobial agents and chemotherapy, 2011, 55(8):3861-3869.
Ramon-Garcia S, et al., "Measurements of the in vitro antimycobacterial activity of ivermectin are method-dependent", J Antimicrob Chemother, 2014, 69(6):1723-4.
Ramón-García S. et al., "Measurements of the in vitro antimycobacterial activity of ivermectin are method-dependent—authors' response", J Antimicrob Chemother., 2014, 69(6):1725-6.

(Continued)

*Primary Examiner* — Layla Bland
(74) *Attorney, Agent, or Firm* — Carol L. Francis; Bozicevic, Field & Francis LLP

(57) ABSTRACT

The present invention relates to methods of treating a mycobacterial infection. In particular, this invention relates to methods, uses and compounds for use in treating mycobacterial infections, including *tuberculosis*. For example, the compounds may be an avermectin or a milbemycin. The avermectin or milbemycin may be selected from, but not limited to, one or more of ivermectin, moxidectin or selamectin. Exemplary microbial infections that may be treated include, but are not limited to, infections caused by *Mycobacterium tuberculosis*, *Mycobacterium bovis*, other *mycobacteria* of the *tuberculosis* complex, and non-tuberculous *mycobacteria*, including *Mycobacterium ulcerans*.

21 Claims, 27 Drawing Sheets

(56) References Cited

PUBLICATIONS

Ramon-Garcia S, et al. "Repurposing avermectins as new potential TB therapies", 16$^{th}$ International Congress on Infectious Diseases, Cape Town, South Africa, Abstract, Apr. 2-5, 2014.

Roux, AL. et al., "Multicenter study of prevalence of nontuberculous mycobacteria in patients with cystic fibrosis in France", Journal of clinical microbiology, 2009, 47:4124-4128.

Shoop, W.L. et al., "Structure and activity of avermectins and milbemycins in animal health", Veterinary Parasitology, 1995, 59:139-156.

Ivermectin

Moxidectin

Selamectin

Doramectin

AVERMECTINS AND MILBEMYCINS AS ANTI-MYCOBACTERIAL AGENTS

CROSS REFERENCE TO RELATED APPLICATION

This application claims the benefit of U.S. Provisional Patent Application Ser. No. 61/812,979 entitled "AVERMECTINS AND MILBEMYCINS AS ANTI-MYCOBACTERIAL AGENTS" filed on 17 Apr. 2013, which application is incorporated herein by reference in its entirety.

FIELD OF THE INVENTION

This invention relates to new methods of treating mycobacterial infections. In particular, this invention relates to methods and pharmaceutical formulations for treating mycobacterial infections including, but not limited to, drug-susceptible, multidrug resistant, extensively drug resistant and totally drug resistant strains.

INTRODUCTION

Microbial or bacterial infections occur when a bacterial species colonizes a host, such as a human. Bacteria are capable of replicating outside host cells, for example in the circulation, in extracellular connective tissues, and in various tissue spaces such as the airways, and intestinal lumens.

Bacterial infections are a source of concern for human health as well as for other animals and organisms that are infected by bacteria. For example, the World Health Organization estimated that approximately 1.3 million people died worldwide in 2012 from *tuberculosis* (TB), an infection caused by *Mycobacterium tuberculosis*.

Antibiotic resistance systems allow a bacterium to survive exposure to an antibiotic. Some of these systems may also serve physiological functions in addition to antibiotic resistance. Resistance can be increased either by spontaneous or induced genetic mutation in bacteria. Genes that confer resistance can be transferred between bacteria in a horizontal fashion by conjugation, transduction, or transformation. Thus a gene for antibiotic resistance that had evolved via natural selection may be shared. Evolutionary stress such as exposure to antibiotics then selects for the antibiotic resistant trait. Many antibiotic resistance genes reside on plasmids, facilitating their transfer.

In *Mycobacteria*, antibiotic resistance can be acquired or intrinsic. Acquired resistance allows for high-levels of antibiotic resistance (higher than a 64-fold increase). For example, the rpoB gene, that encodes the beta subunit of bacterial RNA polymerase, is the site of numerous mutations that confer resistance to rifampicin. Intrinsic antibiotic resistance may allow for low-levels of antibiotic resistance that might lead to the development of high-levels of resistance by facilitating mutations in genes related to acquired resistance. Systems providing intrinsic antibiotic resistance include, but are not limited to, efflux pump, and antibiotic-modifying enzymes, among others.

*Tuberculosis* (TB)

The current TB regimen recommended for drug-susceptible disease is lengthy (at least 6 months) with a cure rate of 95% under optimal conditions (Koul, A., et al. 2001. The challenge of new drug discovery for *tuberculosis*. Nature 469:483-490). Co-infection with HIV and the emergence of resistant strains has reaffirmed TB as a global public health threat (World Health Organization. 2012. Global *Tuberculosis* Report. Geneva, S.). Multi drug-resistant (MDR) *M. tuberculosis* strains are resistant to rifampin and isoniazid, the two first-line TB drugs; extensively drug-resistant (XDR) *M. tuberculosis* strains have, in addition, acquired resistance to fluoroquinolones, and to any one of the three injectable second-line anti-TB drugs (amikacin, kanamycin or capreomycin) (Jassal, M. and Bishai, W. R. 2009. Extensively drug-resistant *tuberculosis*. Lancet Infect Dis 9:19-30). Totally drug-resistant (TDR) TB strains are resistant to any antibiotic tested (Katherine Rowland (13 Jan. 2012) "Totally drug-resistant TB emerges in India" Nature). Effective MDR-TB therapy is more toxic to patients, costly, prolonged (up to 2 years), and uncertain (cure rates typically range from 50% to 70%) (Koul et al. 2001, supra). All of these problems are even more acute for XDR- and TDR-TB patients, for whom few options are available (Chiang, C. Y., et al. 2010. Drug-resistant *tuberculosis*: past, present, future. Respirology 15:413-432). Accordingly, alternative therapies are urgently needed both to shorten the duration of the current TB treatment, and to treat MDR-TB, XDR-TB and TDR-TB. The WHO has recommended that the term TDR not be used. However, its use herein is meant to refer to any antibiotic and the definition of XDR is more limited in scope.

Development of new therapies for bacterial infections has traditionally focused on empirical screening for single compounds that inhibit growth. As identification of active new compounds using this approach became less fruitful, pharmaceutical companies embarked on massive target-based high-throughput screening campaigns. This approach proved to be a lengthy process, with unsustainably low yields and profits (Payne, D. J. et al. 2007. Drugs for bad bugs: confronting the challenges of antibacterial discovery. Nat. Rev. Drug Discov. 6:29-40). One possible solution is to identify new uses for existing drugs (Boguski, M. S. et al. 2009. Drug discovery. Repurposing with a difference. Science 324:1394-1395.), either alone or in combination therapies. Since approved drugs have known pharmacokinetic and safety profiles, any newly identified application can be more rapidly evaluated, thereby decreasing the average development time (Chong, C. R., and D. J. Sullivan, Jr. 2007. New uses for old drugs. Nature 448:645-646).

Avermectins and Milbemycins

The avermectins are a series of 16-membered macrocyclic lactone derivatives with potent anthelmintic and insecticidal properties. The milbemycins are a group of macrolides chemically related to the avermectins. They are used in veterinary medicine as antiparasitic agents against worms, ticks and fleas. They have a similar mechanism of action, but a longer half-life than the avermectins. Both families of drugs open glutamate-sensitive chloride channels in neurons and myocytes of invertebrates, leading to hyperpolarisation of these cells and blocking of signal transfer, which leads to paralysis of the somatic muscles, particularly the pharyngeal pump, causing the death of the parasite. Related chloride ion receptors are found in neurons of the mammalian the central nervous system (less exposed to these drugs), whereas in arthropods and nematodes they are located in the peripheral nervous system. Accordingly, these compounds are well suited for administration to mammals to treat arthropod and nematode infections.

SUMMARY

This invention is based, in part, on the discovery that avermectin and milbemycin compounds, as described herein, have anti-mycobacterial activity. Specifically, abamectin, doramectin, emamectin, eprinomectin, ivermectin, milbemycin oxime, moxidectin and selamectin are shown to have anti-*tuberculosis* activity, which may be useful for the treatment or prophylaxis of infection. In particular, the treatment or prophylaxis of *tuberculosis*. The infection may be *tuberculosis*. The infection may be a *M. tuberculosis* infection. The infection may be caused by a multi-drug resistant strain of *Mycobacterium tuberculosis* (MDR-, XDR- and TDR-TB). The infection may be a *M. bovis* infection. The infection may be a *M. leprae* infection. The infection may be a *M. avium* infection. The infection may be a *M. ulcerans* infection. The infection may be caused by a slow growing *mycobacteria*. The slow growing *mycobacteria* may be *M. ulcerans*. The infection may be may be caused by a rapid growing *mycobacteria*. The infection may also be caused by other *mycobacteria*, as well, including, but not limited to *M. bovis*, another *mycobacterium* of the *tuberculosis* complex (e.g., *M. africanum, M. canetti, M. microti*), or a non-tuberculous *mycobacteria*, such as, but, not limited to *M. ulcerans, M. avium intracellulare, M. kansasii, M. fortuitum, M. chelonae, M. marinum* and *M. leprae*. The infection may be *M. tuberculosis*. The infection may be *M. bovis*. The infection may be *M. leprae*. The infection may be *M. avium* (including *Mycobacterium avium* subsp. *paratuberculosis*).

This invention is based in part on the discovery that an avermectin compound, as described herein, may have anti-mycobacterial properties when administered, as described herein. Specifically, the compounds identified herein, show anti-*tuberculosis* activity, which may be useful for the treatment or prophylaxis of infection. In particular, the treatment or prophylaxis may be of mycobacterial infections. In particular, the treatment or prophylaxis may be of *tuberculosis*.

In accordance with one embodiment, there is provided a method of treating a mycobacterial infection, the method including administering at least one avermectin compound or at least one milbemycin compound or analogs or derivatives thereof, to a subject in need thereof.

In accordance with another embodiment, there is provided a use of at least one avermectin compound or at least one milbemycin compound or analogs or derivatives thereof in the manufacture of a medicament for the treatment of a mycobacterial infection.

In accordance with another embodiment, there is provided a use of at least one avermectin compound or at least one milbemycin compound or analogs or derivatives thereof for the treatment of a mycobacterial infection.

In accordance with another embodiment, there is provided an at least one avermectin compound or an at least one milbemycin compound or analogs or derivatives thereof for use in the treatment of a mycobacterial infection.

The at least one avermectin or at least one milbemycin compound may be selected from one or more of the following: abamectin; emamectin; eprinomectin; doramectin; ivermectin; selamectin; milbemectin; milbemycin oxime; moxidectin; and nemadectin; or analogs or derivative of any of the preceding. The at least one avermectin or milbemycin compound may be selected from abamectin, doramectin, emamectin, eprinomectin, ivermectin, milbemycin oxime, moxidectin and selamectin. The at least one avermectin or milbemycin compound may be abamectin. The at least one avermectin or milbemycin compound may be doramectin. The at least one avermectin or milbemycin compound may be emamectin. The at least one avermectin or milbemycin compound may be eprinomectin. The at least one avermectin or milbemycin compound may be ivermectin. The at least one avermectin or milbemycin compound may be milbemycin oxime. The at least one avermectin or milbemycin compound may be moxidectin. The at least one avermectin or milbemycin compound may be selamectin.

The mycobacterial infection may be *tuberculosis*. The *tuberculosis* may be caused by non-*M. tuberculosis mycobacteria*. The organism responsible for the mycobacterial infection may be a non-*M. tuberculosis* MDR, a non-*M. tuberculosis* XDR, or a non-*M. tuberculosis* TDR strain. The mycobacterial infection may be a *M. tuberculosis* infection, a *M. bovis* infection, or a *M. fortuitum* infection. The organism responsible for the mycobacterial infection may be *M. tuberculosis*. The organism responsible for the mycobacterial infection may be MDR-*M. tuberculosis*, XDR-*M. tuberculosis*, or TDR-*M. tuberculosis*. The subject may have *tuberculosis*. The organism responsible for the mycobacterial infection may be *M. bovis*. The organism responsible for the mycobacterial infection may be *M. fortuitum*. The organism responsible for the mycobacterial infection may be *Mycobacterium ulcerans* or *M. leprae* or *M. avium* or *M. marinum*. The organism responsible for the mycobacterial infection may be *M. ulcerans*. The organism responsible for the mycobacterial infection may be *M. leprae*. The organism responsible for the mycobacterial infection may be *M. avium*. The organism responsible for the mycobacterial infection may be *M. marinum*. The organism responsible for the mycobacterial infection may be *Mycobacterium avium* subsp. *paratuberculosis*. The organism responsible for the mycobacterial infection may be a *mycobacterium* of the *tuberculosis* complex. The organism responsible for the mycobacterial infection may be *M. africanum*, or *M. canetti*, or *M. microti*. The organism responsible for the mycobacterial infection may be a non-tuberculous *mycobacteria*. The organism responsible for the mycobacterial infection may be *M. ulcerans*, or *M. avium intracellulare*, or *M. kansasii*, or *M. fortuitum*, or *M. chelonae*, or *M. leprae*, or *M. abscessus*, or *M. marinum*. The infection may be caused by a slow growing *mycobacteria*. The infection may be caused by a rapid growing *mycobacteria*. The organism responsible for the mycobacterial infection may be *M. avium intracellulare, M. avium, M. kansasii, M. fortuitum, M. abscessus*, or *M. marinum*.

The subject may be a mammal. The subject may be a rat, mouse, dog, cat, cow, sheep, horse, pig or primate. The subject may be a human. The subject may be a cow. The cow may have a mycobacterial infection that is a *Mycobacterium avium* subsp. *paratuberculosis*. The cow may have Johne's disease.

This invention is based in part on the discovery that an avermectin compound, as described herein, may have anti-mycobacterial properties when administered, as described herein. Specifically, the compounds identified herein, show enhanced anti-*tuberculosis* activity, which may be useful for the treatment or prophylaxis of infection. In particular, the treatment or prophylaxis of *tuberculosis*. The avermectin may be selected from, but not limited to, one or more of the following: abamectin; emamectin; eprinomectin; doramectin; ivermectin; and selamectin; and analogs and derivatives of any one or more of the preceding. The infection may be *tuberculosis*. The infection may be a *M. bovis* infection. The infection may be a *M. leprae* infection. The infection may be a *M. avium* infection. The infection may be a *M. ulcerans* infection. The infection may be a *M. abscessus* infection. The infection may be a *M. marinum* infection.

This invention is based in part on the discovery that a milbemycin compound, as described herein, may have anti-mycobacterial properties when administered, as described herein. Specifically, the compounds identified herein, show enhanced anti-*tuberculosis* activity, which may be useful for the treatment or prophylaxis of infection. In particular, the treatment or prophylaxis of *tuberculosis*. The milbemycin may be selected, but not limited to, from one or more of the following: milbemectin; milbemycin oxime; moxidectin; and nemadectin; and analogs and derivatives of any one or more of the preceding. The infection may be *tuberculosis*. The infection may be a *M. bovis* infection. The infection may be a *M. leprae* infection. The infection may be a *M. avium* infection. The infection may be a *M. ulcerans* infection. The infection may be a *M. abscessus* infection. The infection may be a *M. marinum* infection.

The compounds described herein may be used for in vivo or in vitro research uses (i.e. non-clinical) to investigate the mechanisms of drug resistance in microorganisms or to test in combination with other compounds. Furthermore, these compounds may be used individually or as part of a kit for in vivo or in vitro research to investigate mechanisms of drug resistance in microorganisms using recombinant proteins, bacterial strains or other microorganisms, cells maintained in culture, and/or animal models. Alternatively, the compounds described herein may be combined with commercial packaging and/or instructions for use.

In accordance with one embodiment, there is provided a method of treating mycobacterial infections, wherein the method includes administering the at least one compound, wherein the at least one compound may be selected from, but not limited to, one or more of the following: abamectin; emamectin; eprinomectin; doramectin; ivermectin; selamectin; milbemectin; milbemycin oxime; moxidectin; and nemadectin; and analogs and derivatives of any one or more of the preceding.

In accordance with another embodiment, there is provided a method of killing *mycobacteria* by administration of one or more avermectin compound or milbemycin compound. Various avermectin and milbemycin compounds show bactericidal activity against *M. tuberculosis*. The method may include contacting a mycobacterial cell with the at least one compound, wherein the at least one compound may be selected from, but not limited to, one or more of the following: abamectin; emamectin; eprinomectin; doramectin; ivermectin; selamectin; milbemectin; milbemycin oxime; moxidectin; and nemadectin; and analogs and derivatives of any one or more of the preceding.

The subject may have a mycobacterial infection. The mycobacterial infection may be *M. leprae, M. tuberculosis, M. bovis, M. avium* (including *Mycobacterium avium* subsp. *paratuberculosis*), *M. ulcerans, M. smegmatis, M. marinum, M. abscessus*, or *M. fortuitum*. The mycobacterial infection may be *M. tuberculosis*. The mycobacterial infection may be MDR-*M. tuberculosis*, XDR-*M. tuberculosis* or TDR-*M. tuberculosis*. The subject may have *tuberculosis*. The subject may have leprosy. The organism responsible for the mycobacterial infection may be *M. leprae, M. tuberculosis, M. bovis*, or *M. fortuitum*. The subject may have *Paratuberculosis* or Johne's disease. The organism responsible for the mycobacterial infection may be *M. tuberculosis*. The organism responsible for the mycobacterial infection may be *M. leprae*. The organism responsible for the mycobacterial infection may be MDR-*M. tuberculosis*, XDR-*M. tuberculosis* or TDR-*M. tuberculosis*. The subject may have *tuberculosis*. The subject may have pulmonary *tuberculosis*. The subject may have miliary *tuberculosis*. The subject may have *tuberculosis* meningitis. The subject may have leprosy.

In accordance with another embodiment, there are provided a pharmaceutical compositions and formulations of an avermectin or a milbemycin for the treatment of mycobacterial infection. The pharmaceutical composition may further include a pharmaceutically acceptable carrier or excipient.

The compounds or compositions described herein may be for use in the treatment of an infection. The compounds or compositions described herein may be for use in the manufacture of a medicament for use in the treatment of an infection. The compounds or compositions described herein may be used for treating infection. The infection may be mycobacterial. The infection may be *tuberculosis*. The infection may be leprosy. The mycobacterial infection may be *M. leprae, M. tuberculosis, M. bovis, M. avium, M. ulcerans, M. abscessus, M. marinum*, or *M. fortuitum*. The mycobacterial infection may be *M. tuberculosis*. The mycobacterial infection may be MDR-*M. tuberculosis*, XDR-*M. tuberculosis* or TDR-*M. tuberculosis*.

BRIEF DESCRIPTION OF THE DRAWINGS

Figure 12A:
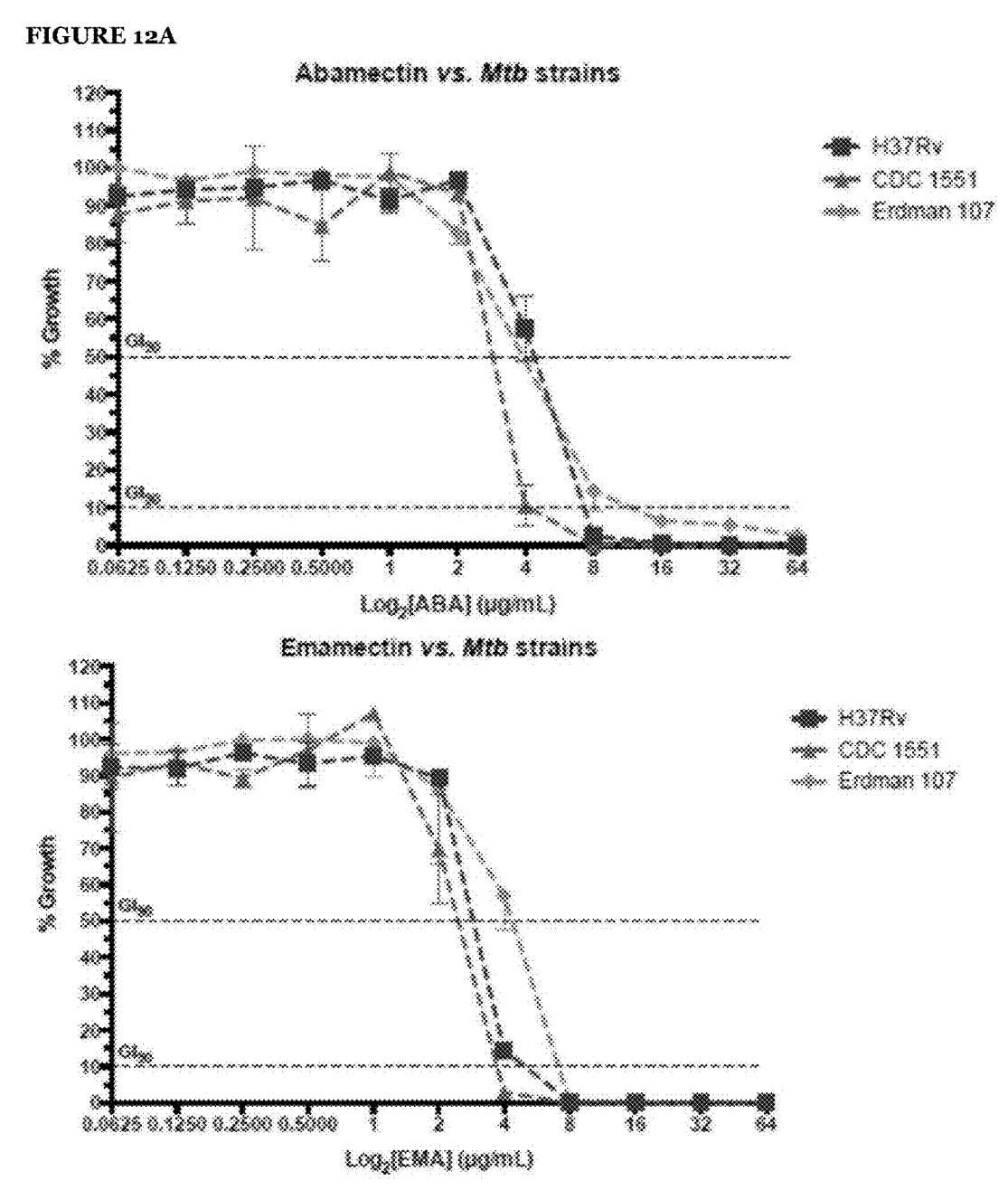
Figure 12C:
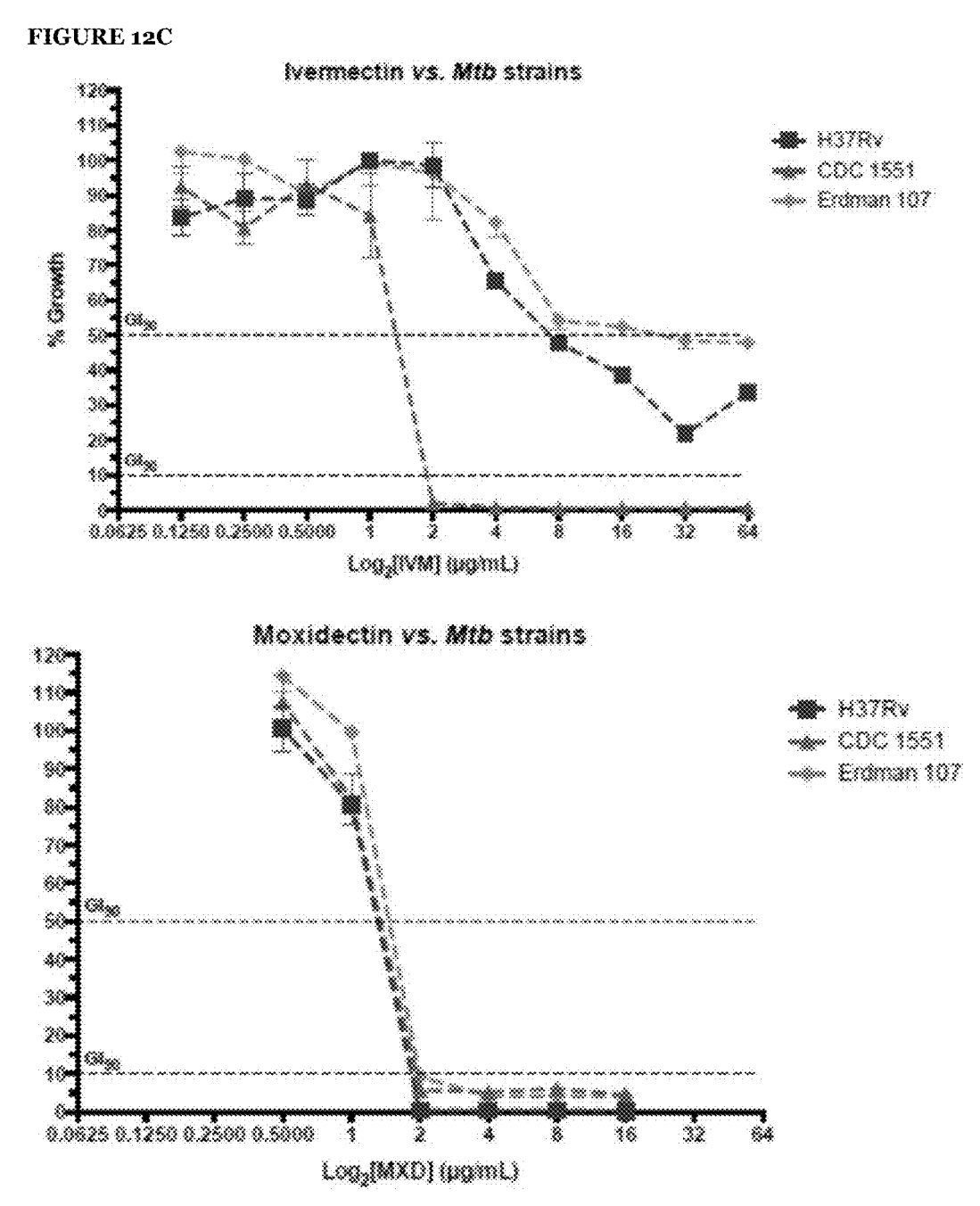

FIGS. 12A-12D shows dose response curves (% growth v. log 2[IVM] (µg/mL)) for avermectin and milbemycin compounds as follows (A) Abamectin and Emamectin; (B) Doramectin and Eprinomectin; (C) Ivermectin and Moxidectin; and (D) Milbemycin oxime and Selamectin against *M. tuber*-

Figure 1:
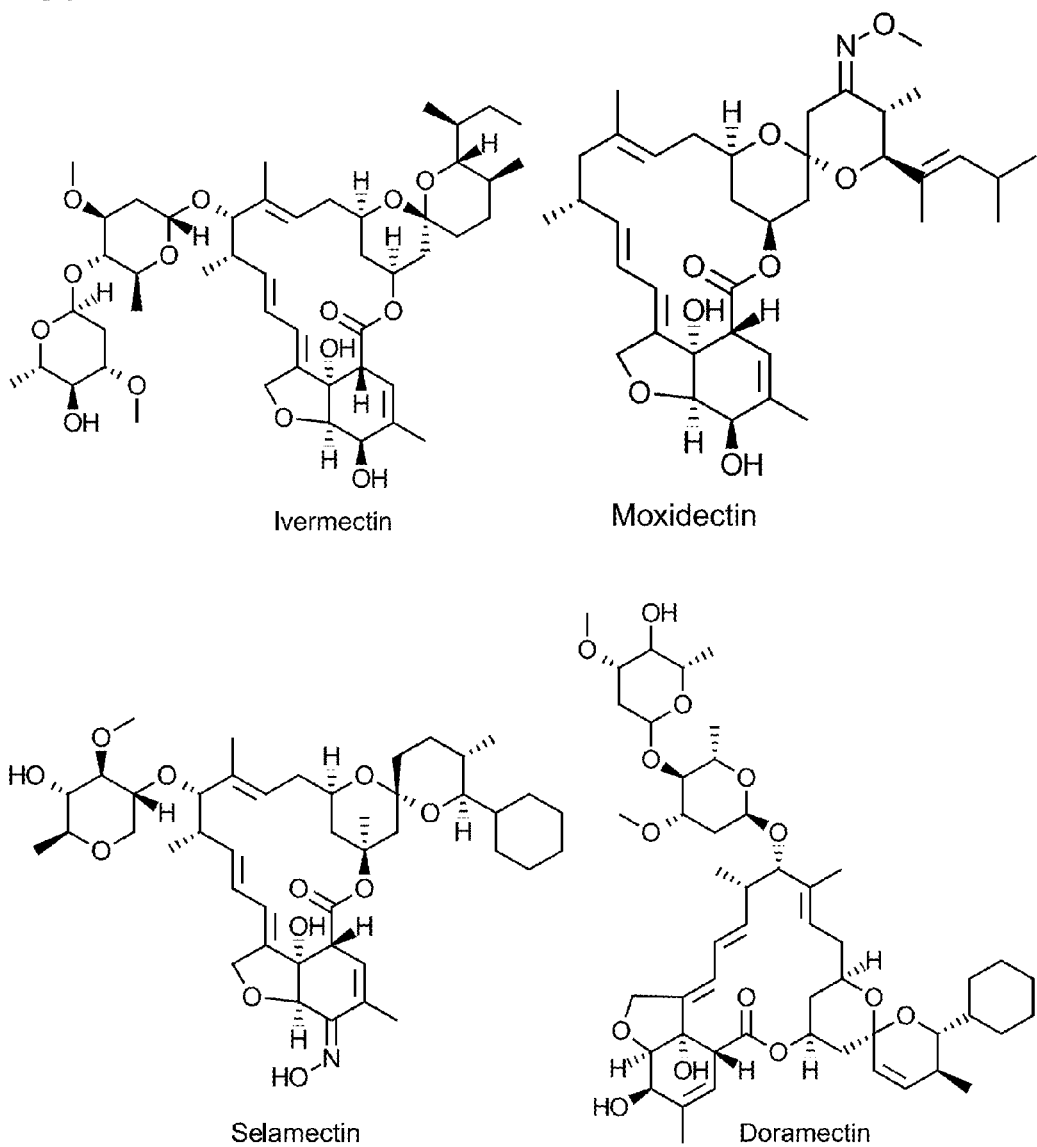
FIG. 1 shows the structure of exemplary avermectin and milbemycin compounds used in the examples.

*culosis* strains (i.e. H37Rv □; CDC 1551 Δ; and Erdman 107 ◇) grown in 7H9+ADC+Glycerol without Tyloxapol in the media.

DETAILED DESCRIPTION

The discovery and development of new drugs for the treatment of TB is a complex process, which to date has provided very few drugs that are clinically effective. To be clinically effective, a drug or a combination of drugs need to disperse tissues in which mycobacterial cells reside, both intracellularly and extracellularly. Furthermore, the mycobacterial target cells residing in these environments may often be in different physiological states, and therefore are likely to have associated differences in drug sensitivities (Dartois V. The path of anti-*tuberculosis* drugs: from blood to lesions to mycobacterial cells. Nature reviews Microbiology 2014; 12: 159-67). So far no single drug in the limited TB drug pool is able to effectively reach and kill all mycobacterial subpopulations in the treatment of TB. Until such drugs are developed, combinations of drugs are likely to be needed and formulations of those drugs may need to be optimized to ensure that therapeutic levels are achieved in at least some of the environments the mycobacterial target cells reside in. Furthermore, drugs may need to be formulated for alternative delivery methods so that therapeutic levels may be achieved at the sites where mycobacterial target cells reside. Therefore, the use of only plasma indices or intracellular activities to discard potential TB drugs as suggested by Ameen and Drancourt (Comment on: Measurements of the in vitro anti-mycobacterial activity of ivermectin are method-dependent. The Journal of antimicrobial chemotherapy 2014) is an oversimplification of the complexities of the pharmacokinetics and pharmacodynamics of anti-bacterial drugs in general and anti-*tuberculosis* drugs in particular. In an era of MDR-, XDR- and even TDR-TB where new drugs are needed every new promising chemical entity must be carefully evaluated (Measurements of the in vitro anti-mycobacterial activity of ivermectin are method-dependent—authors' response. The Journal of antimicrobial chemotherapy 2014).

Ivermectin is approved for human use in many countries to treat onchocerciasis, lymphatic, filariasis, strongiloidiasis, and scabies. Ameen and Drancourt (Comment on: Measurements of the in vitro anti-mycobacterial activity of ivermectin are method-dependent. The Journal of antimicrobial chemotherapy 2014) emphasize that effective dosage levels for these conditions are unusually low and would not be effective for TB treatment. Ivermectin is typically administered once a month at a standard dose of 12 mg (maximal concentration in plasma of ca. 50 ng/mL—Gonzalez Canga A, Sahagun Prieto A M, Diez Liebana M J et al. The pharmacokinetics and interactions of ivermectin in humans—a mini-review. The AAPS journal 2008; 10: 42-6). However, very little is known about the safety and tolerability of higher doses of ivermectin or after more frequent administration. A study in healthy volunteers showed that doses 10 times higher (120 mg) were safe and correlated with higher plasma concentrations (ca. 0.25 µg/mL—Guzzo C A, Furtek C I, Porras A G et al. Safety, tolerability, and pharmacokinetics of escalating high doses of ivermectin in healthy adult subjects. Journal of clinical pharmacology 2002; 42: 1122-33). In fact, the more severe reactions observed in the treatment of onchocerciasis and lymphatic filariasis with ivermectin are most likely secondary immunological effects triggered by the death of the parasite. Thus, higher ivermectin dosage should be explored for TB treatment. Furthermore, we have recently demonstrated that synergistic drug combinations could allow the use of drugs that normally do not inhibit *Mycobacterium tuberculosis* at clinically relevant concentrations (Ramon-Garcia S, Ng C, Anderson H et al. Synergistic drug combinations for *tuberculosis* therapy identified by a novel high-throughput screen. Antimicrobial agents and chemotherapy 2011; 55: 3861-9.). Exploring the synergistic interactions of ivermectin and the other compounds described herein with current anti-TB drugs could allow its use in combinatorial therapies for multidrug (MDR), extensively drug resistant (XDR) and totally drug resistant TB at dosages lower than MIC concentrations of the individual drugs.

In summary, the in vitro anti-mycobacterial activity of the compounds described herein is a first step into the long, complex and challenging process of TB drug selection and development.

Anthelmintics or antihelminthics are compounds that are used for the treatment of parasitic worms (helminths). Examples may be selected from one or more of the following: albendazole; doramectin; mebendazole; moxidectin; thiabendazole; fenbendazole; triclabendazole; flubendazole; abamectin; diethylcarbamazine; niclosamide; ivermectin; selamectin; suramin; pyrantel pamoate; levamisole; praziquantel; emodepside; and monepantel.

'Avermectins' and 'milbemycins' as used herein refer to two related families of anthelmintic compounds. Examples may be selected from one or more of the following: abamectin; emamectin; eprinomectin; doramectin; ivermectin; selamectin; milbemectin; milbemycin oxime; moxidectin; and nemadectin. The avermectins and milbemycins are closely related 16-membered macrocyclic lactones (i.e. a macrocyclic lactone disaccharide). Both chemical groups are produced through fermentation by soil dwelling actinomycetes from the genus *Streptomyces* and have similar biological activities. The most important structural difference between the two groups is a bisoleandrosyloxy substituent found at the 13-position of the macrolide ring of the avermectins. The milbemycins have no substituent at the 13-position. Essentially, the molecular structures of the two groups are superimposable and the avermectins may be thought of as a glycosylated milbemycin, or of the milbemycins as deglycosylated avermectins (Shoop, W. L. et al. 1995. Structure and activity of avermectins and milbemycins in animal health. Veterinary Parasitology 59: 139-156). Interestingly, the oxime moiety present in milbemycin oxime, moxidectin and selamectin but not in abamectin, emamectin, eprinomectin, ivermectin and doramectin strongly correlates with increased anti-mycobacterial activity.

TABLE 1

Exemplary avermectin and milbemycin compounds.

| Compound | Cas # | Compound Class |
|---|---|---|
| Ivermectin | 70288-86-7 | avermectin |
| Selamectin | 220119-17-5 | avermectin |
| Doramectin | 117704-25-3 | avermectin |
| Moxidectin | 113507-06-5 | milbemycin |

Bacterial Infection Therapy

Infections treatable by the avermectin and milbemycin compounds described herein may be caused by *mycobacteria*. Examples of microbial infections that may be treated by methods described herein include, but are not limited to, infections caused by *Mycobacterium tuberculosis, Mycobac-*

*terium bovis*, other *mycobacteria* of the *tuberculosis* complex, and non-tuberculous *mycobacteria*, including *Mycobacterium ulcerans*.

A mycobacterial infection may be a *tuberculosis* infection. The infection may be a *M. tuberculosis* infection. The infection may be caused by a multi-drug resistant strain of *Mycobacterium tuberculosis* (MDR-, XDR-, and TDR-TB). The infection may be a *M. bovis* infection. The infection may be a *M. leprae* infection. The infection may be a *M. avium* infection. The infection may be a *M. ulcerans* infection. The infection may be caused by a slow growing *mycobacteria*. The infection may be may be caused by a rapid growing *mycobacteria*. The infection may also be caused by other *mycobacteria*, as well, including, but not limited to *M. bovis*, another *mycobacterium* of the *tuberculosis* complex (e.g., *M. africanum*, *M. canetti*, *M. microti*), or a non-tuberculous *mycobacteria*, such as, but, not limited to *M. ulcerans*, *M. avium intracellulare*, *M. kansasii*, *M. fortuitum*, *M. chelonae*, *M. marinum* and *M. leprae*. For example, *M. avium* can cause Johne's disease in cattle.

Non-Tuberculous *Mycobacterium* (NTM) infections are found in patients with chronic lung diseases, such as cystic fibrosis (CF) or HIV, and patients that are recovering from surgical procedures. The presence of NTM in CF patients worldwide ranges from 2-28% see references in (Olivier, K N. et al., (2004) Paediatric respiratory reviews 5 Suppl A, S213-216; and Griffith, D E. et al., American Thoracic Surgery and Infectious Disease Society of, A. (2007) 175, 367-416); a recent study reported 8.2% in Canada (Radhakrishnan, D K. et al. (2009) Pediatric pulmonology 44, 1100-1106). Many NTMs are found in diverse environments, but some are becoming human pathogens. One species in particular, *Mycobacterium abscessus*, is most frequently isolated from infants (Roux, A L. et al., (2009) Journal of clinical microbiology 47, 4124-4128) and older patients with chronic lung diseases (see references in (Bryant, J. M. et al. (2013) Lancet 381, 1551-1560)) or HIV (Parrish, S. C., Myers, J., and Lazarus, A. (2008) Postgraduate medicine 120, 78-86). The evolving virulence genes of *M. abscessus* allows it to infect and cause severe and often fatal pathology in apparently healthy people (30% of isolates) (Griffith, D. E., Girard, W. M., and Wallace, R. J., Jr. (1993) The American review of respiratory disease 147, 1271-1278), especially middle aged and older women. Patient-to-patient transmissions of *M. abscessus* have been documented. Only two antibiotics can be used to treat CF patients infected with NTM (amikacin and clarithromycin), but common resistance mutations limit the use of these treatments. Another species, *M. marinum*, a non-tuberculous *mycobacterium* found in non-chlorinated water, with worldwide prevalence, is the most common atypical *Mycobacterium* that causes opportunistic infection in humans. Typically, it presents as a cutaneous infection although deeper infections might also occur. There have been many therapeutic modalities used effectively in the treatment of *M. marinum* infections. However, there is no proven treatment of choice because *M. marinum* is naturally multi-drug resistant species and treatment is based primarily on the personal experience and preference of individual investigators, without the benefit of large studies. (Rallis E1, Koumantaki-Mathioudaki E. (2007) Expert Opin Pharmacother. December; 8(17):2965-78. Treatment of *Mycobacterium marinum* cutaneous infections.)

A "subject", as used herein, refers to a patient, for example a human patient. The subject may have been previously diagnosed with a bacterial infection, or may be suspected of having a bacterial infection and thus may be a candidate for antibiotic treatment. Alternatively, the subject may be a non-human animal, such as a bird or a mammal. Specific animals may include rat, mouse, dog, cat, cow, sheep, horse, pig or primate. A subject may further be a transgenic animal. A subject may further be a rodent, such as a mouse or a rat. The subject may be a cow. The subject may be a human.

Some of the methods disclosed herein may be useful for treating these microbial infections as described herein, whereby they may inhibit the onset, growth, or spread of the microbial infection, may cause regression of the microbial infection, may cure the microbial infection, or may otherwise improve the general well-being of a subject afflicted with, or at risk of, contracting the microbial infection. Accordingly, the terms "treat", "treating", and grammatical variations thereof, as well as the phrase "method of treating", are meant to encompass any desired therapeutic intervention, including but not limited to a method for treating an existing microbial infection in a subject, and a method for the prophylaxis (i.e., preventing) of a microbial infection, such as in a subject that has been exposed to a microbe as disclosed herein or that has an expectation of being exposed to a microbe as disclosed herein.

The compounds described herein may be used in isolation, or may be linked to or in combination with liposomes, carbohydrate carriers, polymeric carriers or other agents or excipients as will be apparent to one of skill in the art. In an alternate embodiment, such compounds may comprise a medicament, including other antibiotics, wherein such compounds may be present in a pharmacologically effective amount.

Compositions or compounds according to some embodiments may be administered in any of a variety of known routes. Examples of methods that may be suitable for the administration of a compound include oral, intravenous, inhalation, intramuscular, subcutaneous, topical, intraperitoneal, intra-rectal or intra-vaginal suppository, sublingual, and the like. The compounds of the present invention may be administered as a sterile aqueous solution or oil solution (for example, sesame, corn, soybean oil or other acceptable oil), or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds may vary depending on the route of administration (for example, oral, intravenous, inhalation, or the like) and the form in which the composition or compound is administered (for example, solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art.

According to some embodiments, prodrugs of the compounds as described herein are also provided. Those of ordinary skill in the art will appreciate that prodrugs are compounds which are converted to the compounds as described herein or salts thereof under specified conditions. Specified conditions may include, for example, and without limitation, in vivo enzymatic or non-enzymatic means. Conversion of the prodrug may occur, for example, and without limitation, spontaneously, or it may be catalyzed, induced by another agent, or a change in a physical parameter or environmental parameter, for example, an enzyme, light, acid, temperature or pH. In some embodiments, the prodrug may have little or no pharmacological activity themselves, and then when converted into the compounds as described herein have the desired activity. Prodrugs may be prepared, for example, and without limitation, by converting appropriate functional groups (for example, a carboxylic acid functional group —COOH, an alcohol functional group —OH, or primary or secondary amine functional group) in the compounds as described herein with suitable moieties. Suitable moieties would be understood to and can be determined by those of ordinary skill in the art. For example, and without limitation, a prodrug can be formed by converting a primary or secondary amino functionality to an amide functionality. For example, and without limitation, a prodrug can be formed by converting a carboxylic acid functionality to an ester functionality, or converting an alcohol functionality to an ether functionality. A prodrug moiety may be, for example, and without limitation, a protecting group that acts to mask a functional group, a group that acts as a substrate for one or more active or passive transport mechanism, or a group that acts to impart or enhance a property of the compound, for example, solubility, bioavailability or localization. In some embodiments, the compounds as described herein or salts thereof may themselves be prodrugs of other compounds as described herein.

Compounds as described herein may be in the free form or in the form of a salt thereof. In some embodiments, compounds as described herein may be in the form of a pharmaceutically acceptable salt, which are known in the art (Berge et al., 1977. *J. Pharm. Sci.* 66:1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association with the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

Avermectins and Milbemycins

The structures of a few exemplary avermectins and milbemycins are provided in FIG. 1. As used herein, avermectins and milbemycins are considered to be compounds, and as such, avermectins and milbemycins are used herein and examples of each compound group are meant to include all salts thereof, analogs and derivatives thereof.

The avermectins and milbemycins are closely related 16-membered macrocyclic lactones (i.e. a macrocyclic lactone disaccharide). Both chemical groups are produced through fermentation by soil dwelling actinomycetes from the genus *Streptomyces* and have similar biological activities. The most important structural difference between the two groups is a bisoleandrosyloxy substituent found at the 13-position of the macrolide ring of the avermectins. The milbemycins have no substituent at the 13-position. Essentially, the molecular structures of the two groups are superimposable and the avermectins may be thought of as a glycosylated milbemycin, or of the milbemycins as deglycosylated avermectins (Shoop, W. L. et al. 1995. Structure and activity of avermectins and milbemycins in animal health. Veterinary Parasitology 59: 139-156). Examples may be selected from one or more of the following: abamectin; emamectin; eprinomectin; doramectin; ivermectin; selamectin; milbemectin; milbemycin oxime; moxidectin; and nemadectin. The avermectins and milbemycins may be used in combination with other antibiotics to treat microbial infections. More specifically, combinations of the avermectins and milbemycins with other antibiotics may be used to treat mycobacterial infections.

The first avermectins were identified in the mid-1970s in an anti-nematode screening program led by Kitasato Institute and the Merck, Sharp, and Dohme (MSD) laboratories. The anti-mycobacterial activity described herein was surprising because the avermectins were thought to be only effective against helminthes and to be inactive against bacteria. In vitro studies were performed by the inventors showing activities for ivermectin, moxidectin, selamectin and doramectin against *M. tuberculosis* clinical isolates, including MDR- and XDR-TB strain (Lim et al. (2013) Anthelmintic Avermectins Kill *Mycobacterium tuberculosis*, Including Multidrug-Resistant Clinical Strains. Antimicrob. Agents Chemother. Vol. 57. p. 1040-1046).

Ivermectin (IVM), an avermectin, is extremely well tolerated, effective, orally active, and associated with long-term safety at the current clinical dose (12 mg single dose). Merck & Co. have made donations of IVM for over 20 years to patients with river blindness in needy areas throughout the world to treat human onchocerciasis and lymphatic filariasis. Clinical studies have shown that it is safe in humans at doses up to 10-fold higher (120 mg). The $LD_{50}$ in mice has been reported as 25 mg/kg body weight. Moxidectin and selamectin are used in veterinary medicine for nematode control in pets and livestock are also known to be safe and well tolerated for these indications.

Moxidectin, a milbemycin, is safe in humans, and has recently completed a phase III clinical trial to compare its efficacy with ivermectin in subjects infected with Onchocerca volvulus [http://clinicaltrials.gov/ct2/show/NCT00790998]. Single doses up to 36 mg have been reported to be safe but not doses of 54 mg. The $LD_{50}$ in mice and rats has been reported as 84 mg/kg body weight and 106 mg/kg body weight, respectively.

Selamectin, an avermectin, has been administered topically, subcutaneously, or orally in the veterinary setting to treat a number of ectoparasite and endoparasite conditions in dogs and cats, but has not been tested for human use. Doses up to 24 mg/kg have been reported to be safe in cats and dogs (if this is extrapolated to a 70 kg adult, this would be a dose of 1,680 mg). Confirming this extrapolation, the $LD_{50}$ in rats and mice could not be demonstrated and was established as >1,600 mg/kg body weight. A toxicity study in female CD1 mice found selamectin to be well tolerated up to 300 mg/kg body weight. A 3-month repeated dose toxicity study in dogs found an oral dose of 40 mg/kg/day to be safe; using the same assumption as above, this corresponds to 2,800 mg/day for humans. In invertebrate nematodes, avermectins and milbemycins specifically bind to glutamate-gated chloride channels present in nerve and muscle cells, causing paralysis and reduced ability to reproduce. In general, macrocyclic lactones have a high margin of safety in mammals because P-glycoprotein or other types of efflux pumps, highly expressed at the blood-brain barrier, efficiently restricts their penetration into the central nervous system. In fact, dogs lacking MDR1 P-glycoprotein (i.e. border collies) have much less tolerance for treatment with macrocyclic lactone compounds. Extra-label use of ivermectin provokes severe signs of neurotoxicity. In contrast, selamectin, and moxidectin at therapeutic doses can safely be administered to dogs having a homozygous MDR1 mutation without any signs of toxicosis.

In some embodiments, ivermectin may be used to treat microbial infections. In other embodiments, ivermectin may be used in combination with other antibiotics to treat microbial infections. In yet further embodiments, ivermectin may be used to treat microbial infections in ternary or higher order combinations of antibiotics. The infection may be mycobacterial. The infection may be *tuberculosis*. The infection may be leprosy. The mycobacterial infection may be *M. leprae, M. tuberculosis, M. bovis, M. avium, M. ulcerans, M. abscessus*, or *M. fortuitum*, or *M. marinum*. The mycobacterial infection may be *M. tuberculosis*. The mycobacterial infection may be MDR-*M. tuberculosis*, XDR-*M. tuberculosis* or TDR-*M. tuberculosis*.

In some embodiments, selamectin may be used to treat microbial infections. In other embodiments, selamectin may be used in combination with other antibiotics to treat microbial infections. In yet further embodiments, selamectin may be used to treat microbial infections in ternary or higher order combinations of antibiotics. The infection may be mycobacterial. The infection may be *tuberculosis*. The infection may be leprosy. The mycobacterial infection may be *M. leprae, M. tuberculosis, M. bovis, M. avium, M. ulcerans, M. abscessus*, or *M. fortuitum*, or *M. marinum*. The mycobacterial infection may be *M. tuberculosis*. The mycobacterial infection may be MDR-*M. tuberculosis*, XDR-*M. tuberculosis* or TDR-*M. tuberculosis*.

In some embodiments, moxidectin may be used to treat microbial infections. In other embodiments, moxidectin may be used in combination with other antibiotics to treat microbial infections. In yet further embodiments, moxidectin may be used to treat microbial infections in ternary or higher order combinations of antibiotics. The infection may be mycobacterial. The infection may be *tuberculosis*. The infection may be leprosy. The mycobacterial infection may be *M. leprae, M. tuberculosis, M. bovis, M. avium, M. ulcerans, M. abscessus*, or *M. fortuitum*, or *M. marinum*. The mycobacterial infection may be *M. tuberculosis*. The mycobacterial infection may be MDR-*M. tuberculosis*, XDR-*M. tuberculosis* or TDR-*M. tuberculosis*.

The compounds described herein may be selected from, but not limited to, at least one or more of the following: abamectin; emamectin; eprinomectin; doramectin; ivermectin; selamectin; milbemectin; milbemycin oxime; moxidectin; and nemadectin.

In some embodiments, the microbial infection may comprise an infection caused by *mycobacteria* including the organism *Mycobacterium tuberculosis*. In some embodiments, the infection may be caused by a multi-drug resistant strain of *Mycobacterium tuberculosis* (MDR-, XDR- and TDR-TB). The infection may also be caused by other *mycobacteria*, as well, including, but not limited to *M. bovis*, another *mycobacterium* of the *tuberculosis* complex (e.g., *M. africanum, M. canetti, M. microti*), *paratuberculosis* (*Paratuberculosis* or Johne's disease, e.g. *M. avium* (including *Mycobacterium avium* subsp. *paratuberculosis*), or a non-tuberculous *mycobacteria*, such as, but, not limited to *M. ulcerans, M. avium intracellulare, M. kansasii, M. fortuitum, M. marinum, M. chelonae*, and *M. leprae*.

TABLE 2

Summary of various pharmacokinetic properties for ivermectin, moxidectin and selamectin.

| Drug | Species | Dose (oral unless indicated) | Cmax (ng/mL) | T½ (days) | AUC (ng * h/ mL) | References (PubMed ID#) |
|---|---|---|---|---|---|---|
| Ivermectin | Humans | 12 mg (165 µg/kg) | 47 | nd | nd | PMID: 12362927 |
| | | 30 mg (347-541 µg/kg) | 85 | 19 h | 2819 | PMID: 18446504 |
| | | 30 mg (fed) | 260 | 15 h | 4564 | |
| | | 90 mg (1031-1466 µg/kg) | 158 | 19 h | 2910 | |
| | | 120 mg (1404-2000 µg/kg) | 247 | 19 h | 4547 | |
| | Dogs | 250 µg/kg | 132 | 80 h | 5600 | PMID: 1496814 |
| | Horses | 200 µg/kg | 44 | 20 h | 3184 | PMID: 12093191 |
| | Mouse (plasma) | 0.2 mg/kg | 20 | 9.3 h | 573 | PMID: 19161460 |
| | Mouse (lung) | 0.2 mg/kg | 20 | nd | nd | |
| Moxidectin | Humans | 3 mg fast | 22.4 | 33.8 | 1442 | PMID: 14517193 |
| | | 9 mg fast | 57.9 | 34.6 | 3024 | |
| | | 18 mg fast | 141 | 22 | 5856 | |
| | | 36 mg fast | 289 | 20.2 | 10824 | |
| | | 36 mg fed | 296 | 25.7 | 14976 | |
| | Dogs | 250 µg/kg | 234 | 621 h | 11800 | ProHeart 6 (moxidectin) - Product profile |
| Selamectin | Dogs males | 6 mg/kg (topical) | 12.72 | 12.14 | 4609 | Stronghold (selamenctin) - Product profile |
| | Dogs female | 6 mg/kg (topical) | 22.65 | 10.73 | 8903 | |
| | Mouse (plasma) | 12 mg/kg | 3714 | 5.5 | 62285.7 | PMID: 19161460 |
| | Mouse (lung) | 12 mg/kg | 7500 | nd | nd | |
| | Rats | 10 mg/kg | >1000 | 10.3 h | nd | Stronghold (selamenctin) - Product profile |
| | Dogs | 24 mg/kg | 7630 | 45.7 h | 227901 | PMID: 12213114 |
| | | 24 mg/kg (topical) | 86.5 | 266 | 15229 | |
| | Cats | 24 mg/kg | 11929 | 97.7 | 1109933 | PMID: 12213114 |
| | | 24 mg/kg (topical) | 5513 | 198 | 743349 | |

These below examples are provided for illustrative purposes, and are not intended to be limiting.

Materials and Methods

Bacterial Growth Conditions.

Mycobacterial strains were cultivated at 37° C. in Middlebrook 7H9 broth supplemented with 10% (v/v) albumin-dextrose-catalase (ADC) (Difco), 0.2% glycerol and 0.05% (v/v) tyloxapol, or on Middlebrook 7H10 (Difco) agar plates supplemented with 10% (v/v) oleic acid albumin-dextrose-catalase (Difco) and 0.2% glycerol. Nonmycobacterial strains (*Escherichia coli*, *Acinetobacter baumannii*, *Pseudomonas aeruginosa*, *Streptomyces lividans*, *Rhodococcus jostii*, *Kocuria rhizophila*, and *Staphylococcus aureus*) were cultivated at 37° C. in LB medium.

Drug Susceptibility Tests.

Mycobacterial strains were assayed in liquid 7H9 media containing 0.2% glycerol and 10% albumin-dextrose-saline. Nonmycobacterial strains were assayed in LB medium. The MTT assay [3-(4,5-dimethylthiazol-2-yl)-2,5-diphenyl tetrazolium bromide] assays (Montoro, E., et al. 2005. Comparative evaluation of the nitrate reduction assay, the MTT test, and the resazurin microtitre assay for drug susceptibility testing of clinical isolates of *Mycobacterium tuberculosis*. J Antimicrob Chemother 55:500-5) was used to determine the concentration that inhibited growth by 90%. Briefly, 2-fold antibiotic serial dilutions were inoculated with a suspension of *mycobacteria* in microtitre plates at 37° C. The plates were incubated for 3 days for *M. smegmatis* or 7 days for *M. tuberculosis*, *M. bovis* BCG or *M. avium*. The MTT reagent was then added to the cells followed by incubation at 37° C. overnight. The formation of the formazan precipitate indicated bacterial growth. All drug sensitivity tests were carried out in at least three independent experiments.

Time-Kill Kinetics of Avermectins Against *M. tuberculosis*.

Two types of experiments were performed (A) Dose titration. Frozen stocks of *M. tuberculosis* H37Rv were cultured in 15 ml of 7H9 broth supplemented with 10% albumin-dextrose-catalase, 0.2% glycerol in standing 25-cm$^2$ tissue culture flasks at 37° C. and 5% CO2 for 3 days before the addition of avermectins. Cultures were agitated only during sampling. (B) Fixed dose strain comparison. Cultures (5 ml) of *M. tuberculosis* H37Rv and mc25857 (an MDR isolate) were pre-grown in shaking 35-ml bottles in 7H9 broth supplemented with 10% ADC, 0.2% glycerol, and 0.05% tyloxapol to an optical density at 600 nm (OD600) of 0.8. To assess drug activity, cultures were washed once in phosphate-buffered saline (PBS), diluted (1/150) in the same medium (without tyloxapol), and grown at 37° C. in shaking 15-ml conical tubes containing ivermectin, selamectin, or moxidectin at 20 µg/ml. Prior to plating, cell clumps were disrupted by sonication and viability was quantified by plating on 7H10 agar supplemented with 10% oleic acid-albumin-dextrose-catalase and 0.2% glycerol. Plates were incubated at 37° C., and colonies were counted after 2 weeks of incubation (microscopically) and reassessed after 4 weeks.

Anti-*Tuberculosis* Activity of Ivermectin and Selamectin Under Different Media Conditions.

*M. tuberculosis* strains H37Rv, CDC 1551 and Erdman 107 were tested against Ivermectin and selamectin in a variety of growth media (i.e. 7H9 broth plus ADC, ADC+Tyloxapol (Tx), ADC+Tween80 (Tw), ADC+Gly (glycerol), ADC+Gly+Tx, ADC+Gly+Tw, OADC, OADC+Tx, OADC+Tw, OADC+Gly, OADC+Gly+Tx, OADC+Gly+Tw). In a 96-well plate format, three technical replicates. 10^5 cells/mL were incubated for 7 days in the presence of 2-fold serial dilutions of ivermectin and selamectin under different medium conditions. MTT was added and plates further incubated for 1 day. SLS was added to solubilize the formazan precipitate and OD580 measured 1 day after. Internal positive (cells, no drug) and negative (no drugs, no cells) controls were included in every plate. OD values were correlated to bacterial growth to calculate % growth under every drug concentration.

Mouse In Vivo TB Model Study.

Mice were low-dose aerosol infected (50-100 bacteria). In the acute model, immune compromised mice were left untreated for 13 days to allow the infection to become established before 9 days of consecutive drug therapy was initiated. Drugs were administered by oral gavage. Log$_{10}$ cfu reductions in the lungs were compared to untreated group. Rifampin was included as an internal control. An ordinary one-way ANOVA Bonferroni's multiple comparisons test was used to calculate p values. A p value<0.05 indicates statistically significant differences compared to the control group (vehicle).

The following examples are provided for illustrative purposes, and are not intended to be limiting, as such.

EXAMPLES

Example 1

Ivermectin, Selamectin, Moxidectin and Doramectin have Anti-Mycobacterial Activity, Including *M. tuberculosis* Drug-Susceptible, Multidrug-Resistant and Extensively Drug Resistant Strains, but not Gram-Positive and Gram-Negative Anti-Bacterial Activity The antibacterial effectiveness of doramectin, ivermectin, moxidectin, and selamectin (FIG. 1) were examined against representative Gram-positive and Gram-negative bacteria (TABLE 3). Inhibitory effects were not observed on any of these bacteria at concentrations as high as 256 µg/ml using the bacterial growth indicator MTT [3-(4,5-dimethylthiazol-2-yl)-2,5-diphenyl tetrazolium bromide]. The avermectins and milbemycins were then tested for their inhibitory activities against various *Mycobacterium* species using the same MTT assay (Table 1). All three avermectins and the milbemycin moxidectin inhibited growth of *Mycobacterium bovis* BCG and *M. tuberculosis* laboratory strains (H37Rv, CDC 1551, and Erdman) at concentrations ranging from 1 to 8 µg/ml. Three of the four also inhibited growth of *Mycobacterium smegmatis* within this concentration range. All three avermectins and the milbemycin moxidectin were less active against *Mycobacterium avium*; doramectin had lower levels of activity against all *Mycobacterium* species.

In order to investigate the potential inclusion of avermectins and milbemycins in the limited repertoire of TB drugs that might be used against drug-resistant strains, the activities of avermectins were also surveyed against multidrug-resistant (MDR) and extensively drug-resistant (XDR) *M. tuberculosis* clinical isolates from different geographical locations (TABLE 3). The MICs of ivermectin, selamectin, and moxidectin were similar against a panel of 27 MDR and XDR clinical isolates having elevated drug resistance profiles including first- and second-line anti-TB drugs, such as ethambutol, ethion-amide, isoniazid, kanamycin, rifabutin, rifampin, p-amino salicylate (PAS), pyrazinamide, and streptomycin. Only three multidrug-resistant (CI15072, CI12081, and BC-MDR2) and two drug-susceptible (BC-DS4 and BC-DS5) strains were less sensitive to ivermectin (MIC$_{90}$=24 µg/ml). Nevertheless, inhibitory activity against these strains was reflected in low MIC$_{50}$ values (<8 μg/ml). Importantly, the sensitivity of these strains to selamectin and moxidectin was unaffected. In summary, the avermectins and the milbemycin moxidectin were as effective against most drug-resistant *M. tuberculosis* clinical isolates as they were against *M. tuberculosis* laboratory strains.

TABLE 3

Antimicrobial activities of doramectin, ivermectin, moxidectin, and selamectin against bacterial species, including multidrug-resistant *M. tuberculosis* clinical isolates[a].

| Species | Strain | Drug resistance profile[b] | In vitro MIC$_{90}$ (μg/mL)[a] | | | |
|---|---|---|---|---|---|---|
| | | | Ivermectin | Selamectin | Moxidectin | Doramectin |
| *E. coli* | O157:H7 | WT | >256 | >256 | >256 | >256 |
| *A. baumannii* | ATCC 1960 | WT | >256 | >256 | >256 | >256 |
| *P. aeruginosa* | PA01 (H103) | WT | >256 | >256 | >256 | >256 |
| *S. lividans* | 1326 | WT | >256 | >256 | >256 | >256 |
| *R. jostii* | RHA1 | WT | >256 | >256 | >256 | >256 |
| *K. rhizophila* | — | WT | >256 | >256 | >256 | >256 |
| *S. aureus* | ATCC 25923 | WT | >256 | >256 | >256 | >256 |
| *M. smegmatis* | mc$^2$155 | WT | 8 | 4 | 4 | 128 |
| *M. bovis* | BCG Pasteur | WT | 4 | 4 | 4 | 8 |
| *M. tuberculosis* | H37Rv | WT | 6 | 3 | 3 | 8 |
| *M. tuberculosis* | CDC 1551 | WT | 4-8 | 1 | 2 | 4-8 |
| *M. tuberculosis* | Erdman | WT | 8 | 2 | 2-4 | 8 |
| *M. tuberculosis* | 1254[c] | WT | 8 | 2-4 | 4 | 8-16 |
| *M. tuberculosis* | H37Rv mc$^2$4977 | INH | 6 | 1.5 | 3 | ND |
| *M. tuberculosis* | CI5447[e] | INH | 1.5 | 1.5 | 0.8-1.5 | ND |
| *M. tuberculosis* | CI5297[e] | INH | 6 | 3 | 6 | ND |
| *M. tuberculosis* | CI5305[e] | INH | 3 | 1.5 | 1.5 | ND |
| *M. tuberculosis* | H37Rv mc$^2$5857 | INH, RIF | 3 | 1.5 | 3 | ND |
| *M. tuberculosis* | H37Rv mc$^2$5858 | INH, RIF | 3 | 1.5 | 3 | ND |
| *M. tuberculosis* | V2475[d] | INH, RIF | 1.5 | 1.5 | 3 | ND |
| *M. tuberculosis* | CI5058[e] | INH, RIF | 6 | 6 | 6 | ND |
| *M. tuberculosis* | CI5324[e] | INH, RIF | 6 | 3 | 3 | ND |
| *M. tuberculosis* | CI5400[e] | INH, RIF | 3 | 3 | 3 | ND |
| *M. tuberculosis* | CI5072[e] | INH, RIF, SM | >24 | 3-6 | 3 | ND |
| *M. tuberculosis* | CI5358[e] | INH, EMB, ETH | 3 | 1.5 | 3 | ND |
| *M. tuberculosis* | CI5459[e] | INH, EMB, ETH | 3 | 1.5-3 | 1.5 | ND |
| *M. tuberculosis* | CI12081[e] | INH, RIF, SM, EMB, ETH | >24 | 3 | 3 | ND |
| *M. tuberculosis* | KZN11[f] | INH, RIF, SM, EMB | 3 | 3 | 3 | ND |
| *M. tuberculosis* | KZN5[f] | INH, RIF, SM, EMB, ETH, KM, PZA | 6 | 3 | 3 | ND |
| *M. tuberculosis* | KZN6[f] | INH, RIF, SM, EMB, ETH, KM, PZA | 6 | 6 | 3 | ND |
| *M. tuberculosis* | KZN12[f] | INH, RIF, SM, EMB, ETH, KM, PZA | 3 | 3 | 1.5 | ND |
| *M. tuberculosis* | KZN14[f] | INH, RIF, SM, EMB, ETH, KM, PZA | 6-12 | 6 | 3-6 | ND |
| *M. tuberculosis* | KZN15[f] | INH, RIF, SM, EMB, ETH, KM, PZA | 6 | 3 | 3 | ND |
| *M. tuberculosis* | KZN16[f] | INH, RIF, SM, EMB, | 3 | 1.5 | 1.5 | ND |

TABLE 3-continued

Antimicrobial activities of doramectin, ivermectin, moxidectin, and selamectin against bacterial species, including multidrug-resistant *M. tuberculosis* clinical isolates[a].

| Species | Strain | Drug resistance profile[b] | In vitro $MIC_{90}$ (μg/mL)[a] | | | |
|---|---|---|---|---|---|---|
| | | | Ivermectin | Selamectin | Moxidectin | Doramectin |
| *M. tuberculosis* | BC-DS1[g] | ETH, KM, PZA | 4-16 | 2 | 4 | ND |
| *M. tuberculosis* | BC-DS3[g] | — | 8-16 | 1-2 | 2 | ND |
| *M. tuberculosis* | BC-DS4[g] | — | 64 (8) | 1-2 | 2 | ND |
| *M. tuberculosis* | BC-DS5[g] | — | >128 (8) | 2-4 | 2-4 | ND |
| *M. tuberculosis* | BC-MDR2[g] | INH, RIF, PZA, SM, RBT | >128 (8) | 2 | 2-4 | ND |
| *M. tuberculosis* | BC-MDR3[g] | INH, RIF, RBT | 1-2 | 0.5-1 | 1-2 | ND |
| *M. tuberculosis* | BC-MDR4[g] | INH, RIF, EMB, PZA, RBT | 4-16 | 2 | 2-4 | ND |
| *M. tuberculosis* | BC-MDR5[g] | INH, RIF, PZA, SM, PAS, RBT | 4-16 | 2 | 2-4 | ND |

Example 2

Ivermectin, Moxidectin and Selamectin are Bactericidal In Vitro Against *M. tuberculosis*

Figure 2A:
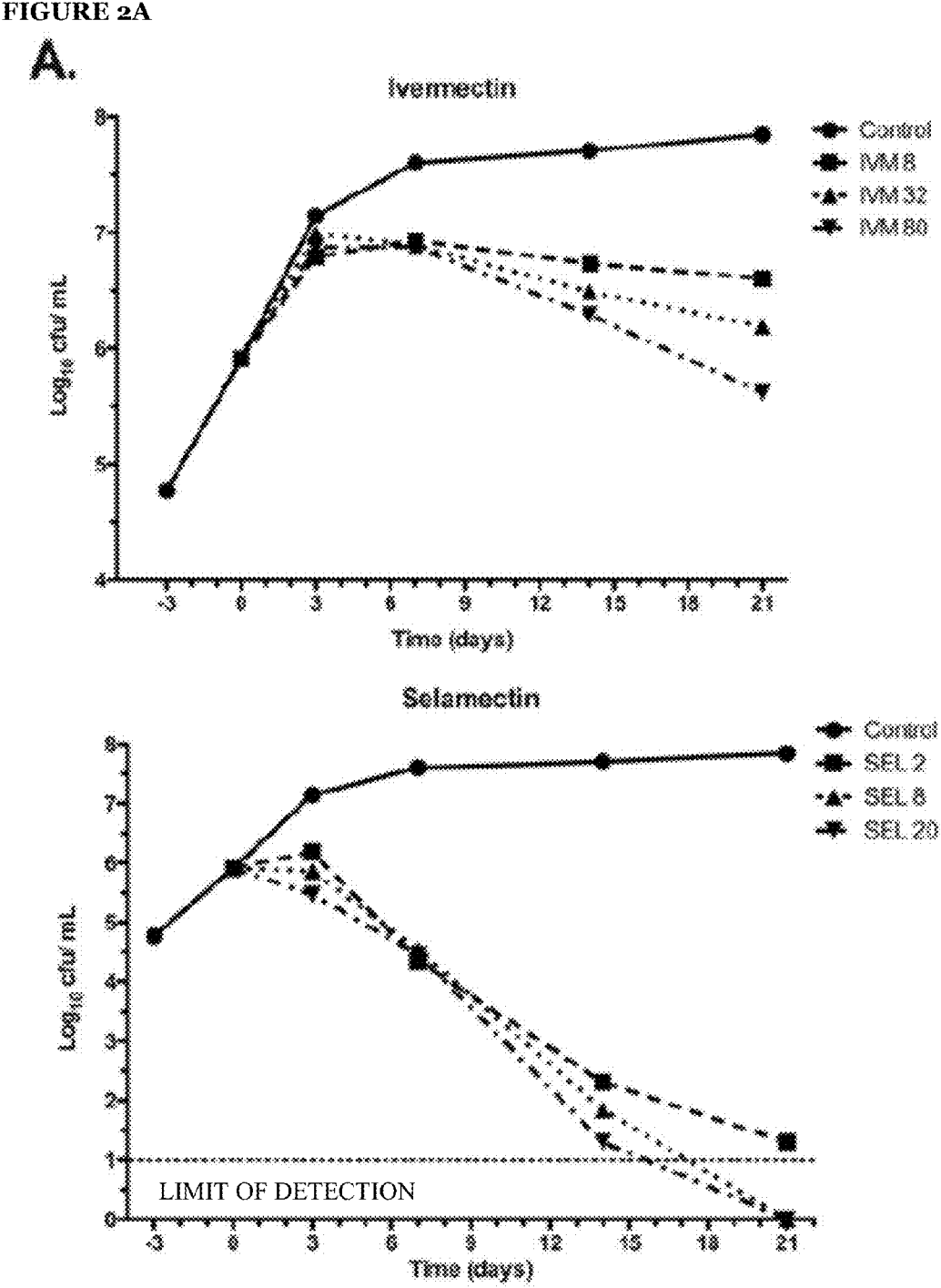
FIG. 2 shows time-kill kinetics of some compounds described herein against *M. tuberculosis*. In (A) dose titrations of ivermectin (IVM), selamectin (SEL), and moxidectin (MXD) at 2, 8, and 20 µg/ml were compared to a control in *M. tuberculosis* cultures. In (B) fixed dose (20 µg/ml of IVM, SEL, and MXD) experiments were carried out on *M. tuberculosis* H37Rv and mc25857 (an MDR isolate).
Figure 2A:
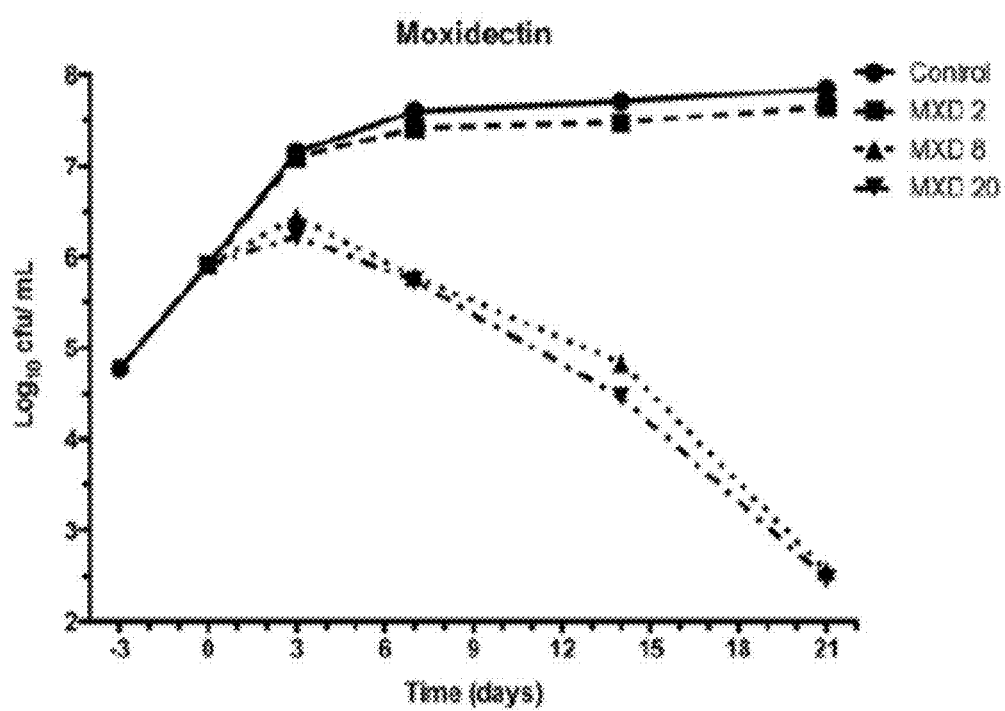
Figure 2B:
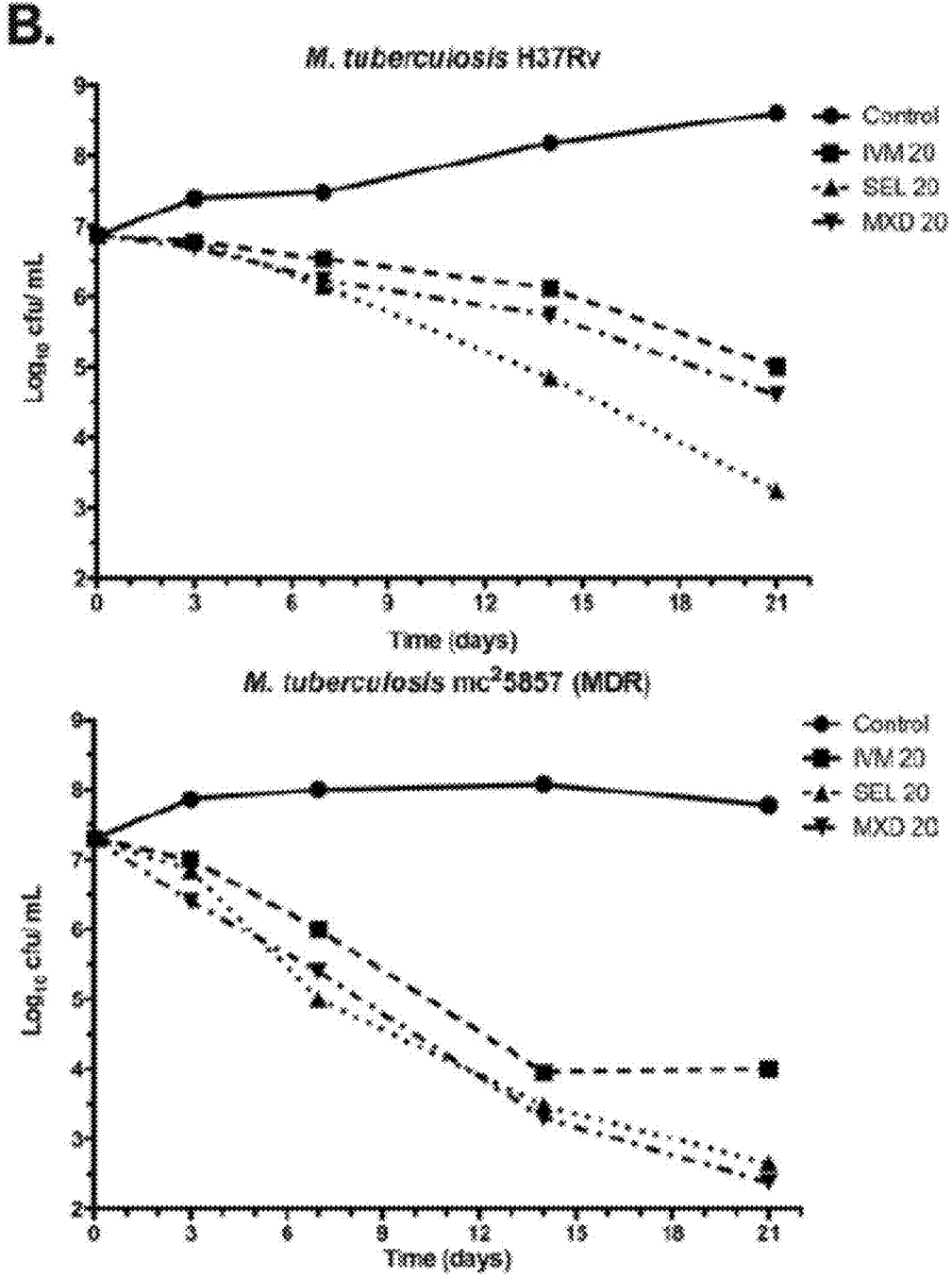
Figure 3:
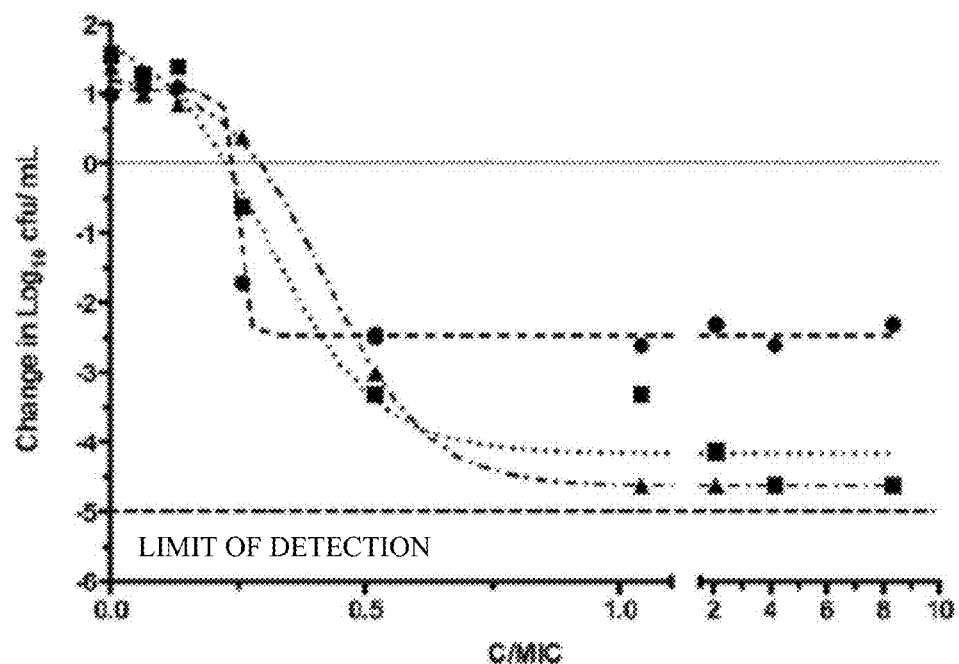
FIG. 3 shows in vitro pharmacodynamics calculations of the effect of concentration and exposure on the bactericidal activities of ivermectin (IVM), selamectin (SEL), and moxidectin (MXD) against *M. tuberculosis*. And shows a comparison of concentration and area under the curve over MIC ratios (C/MIC and AUC/MIC, respectively) on the bactericidal activities of the IVM, SEL, and MXD, where the bactericidal effect was calculated on the basis of the initial inoculum prior to the addition of the anti-mycobacterial agent.
Figure 3:
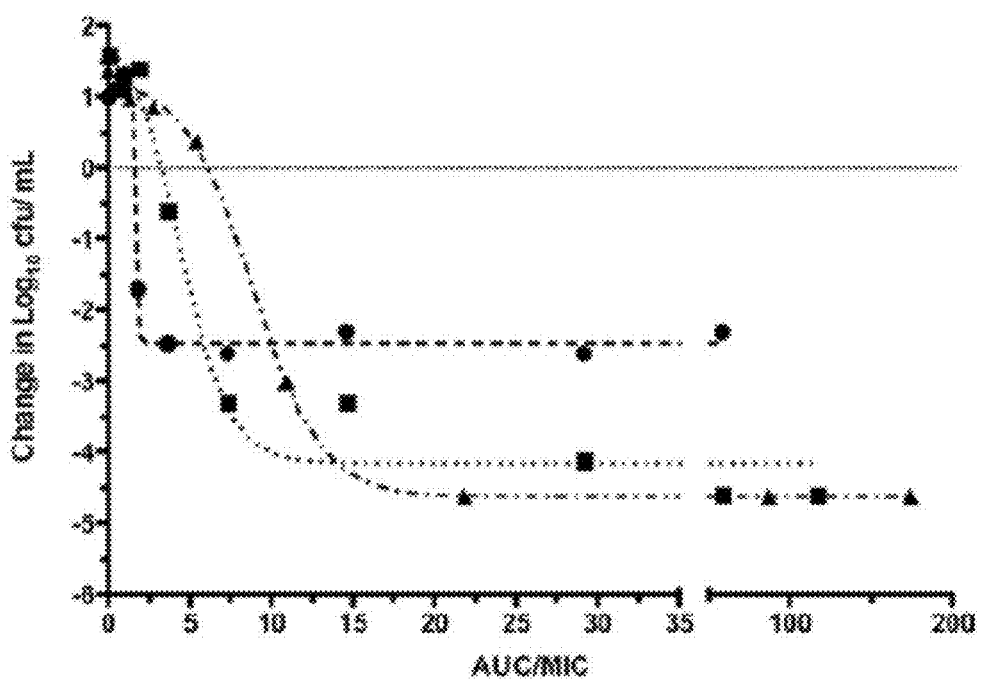
Figure 3:
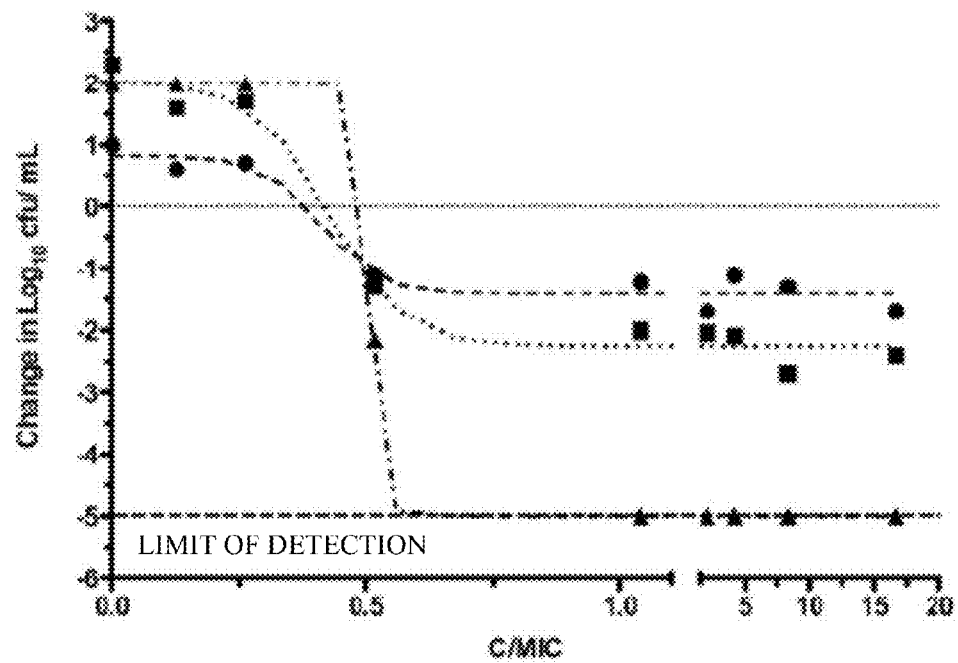
Figure 3:
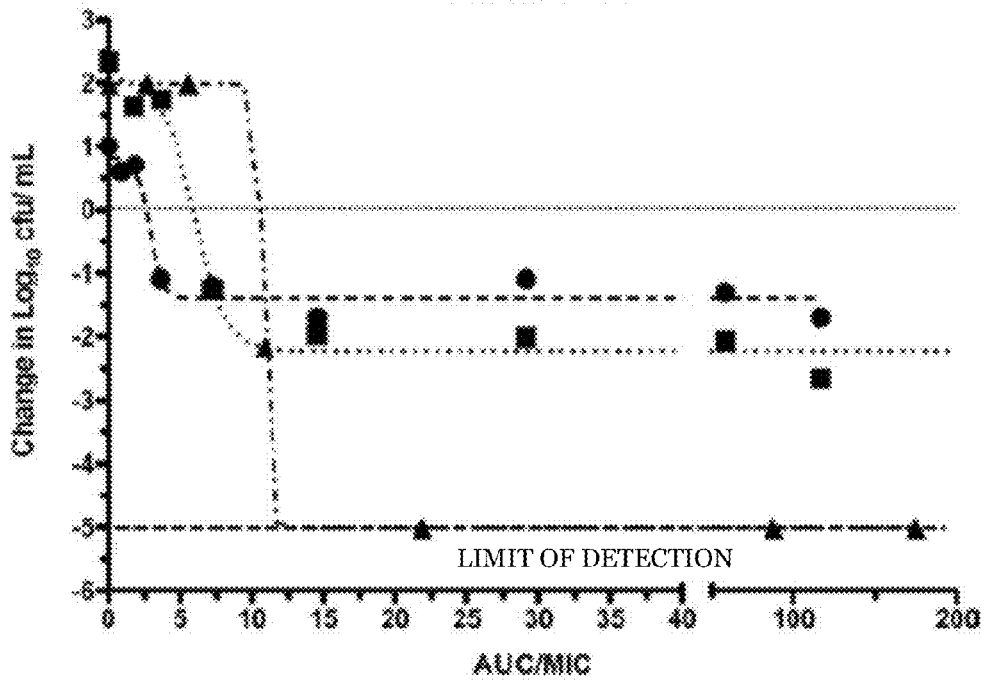
Figure 3:
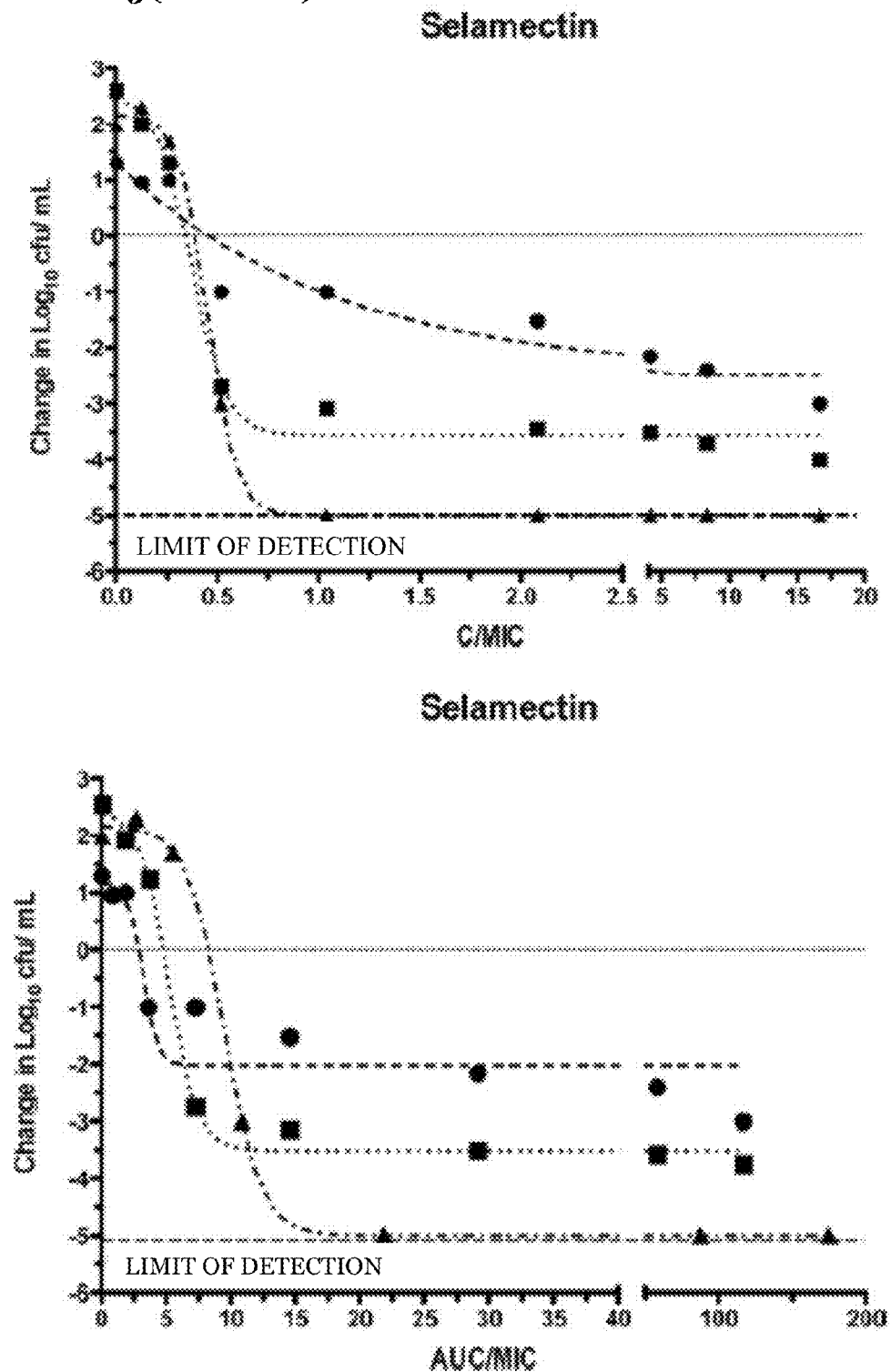
Figure 4A:
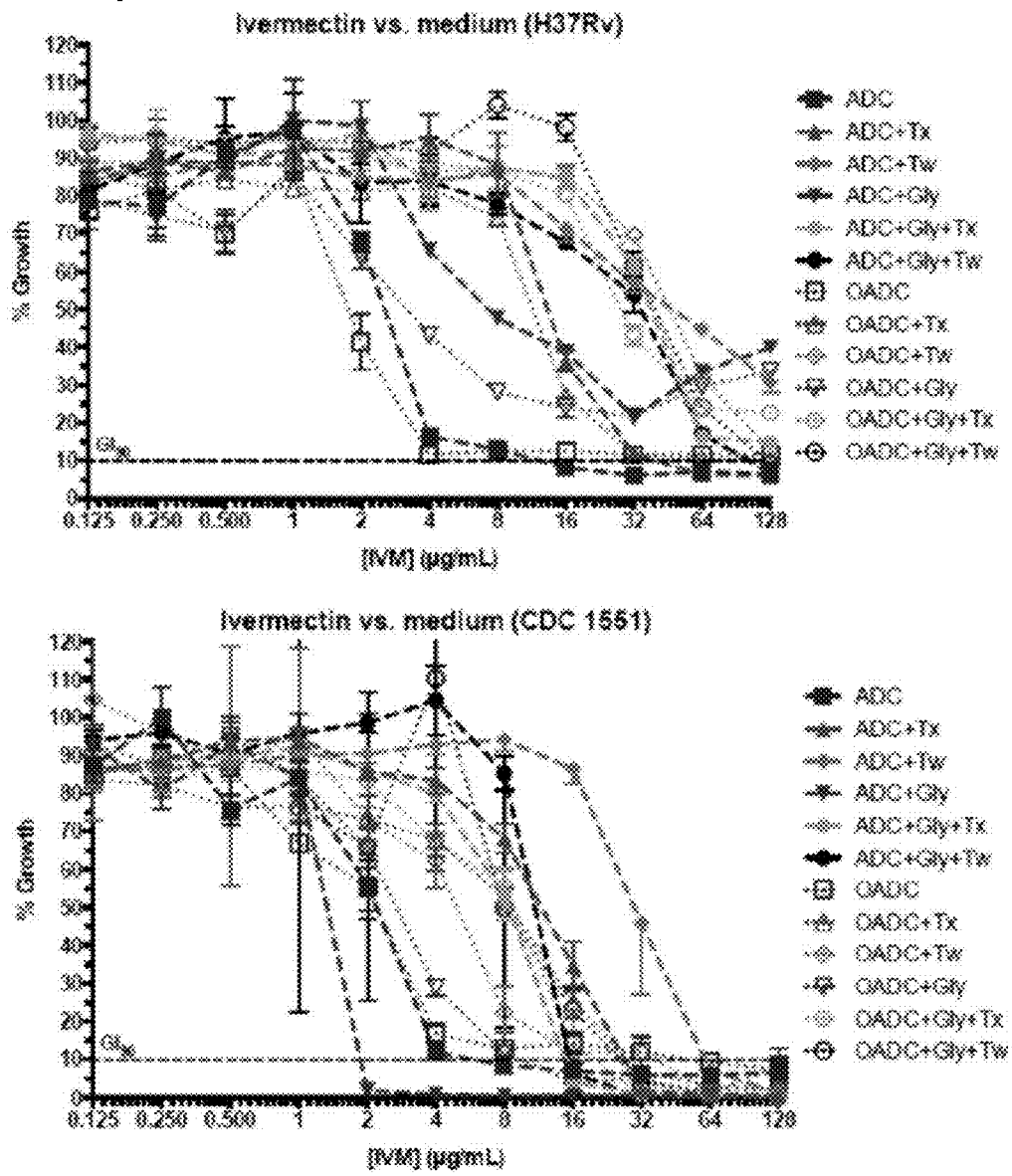
FIGS. 4A-4B shows the anti-*tuberculosis* activity of (FIG. 4A) ivermectin and (FIG. 4B) selamectin under different media conditions against *M. tuberculosis* strains H37Rv; CDC 1551; and Erdman 107.
Figure 4A:
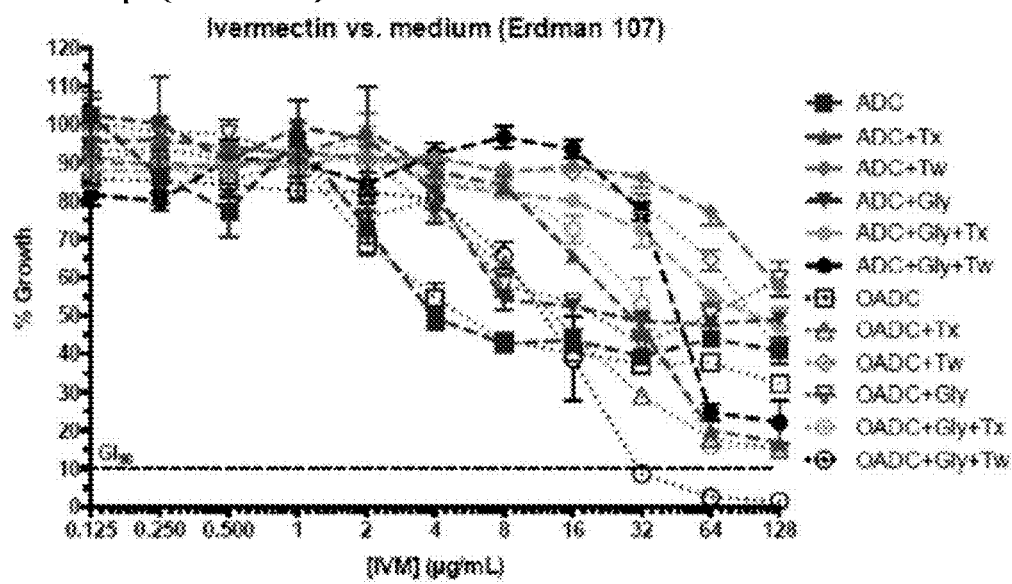
Figure 4B:
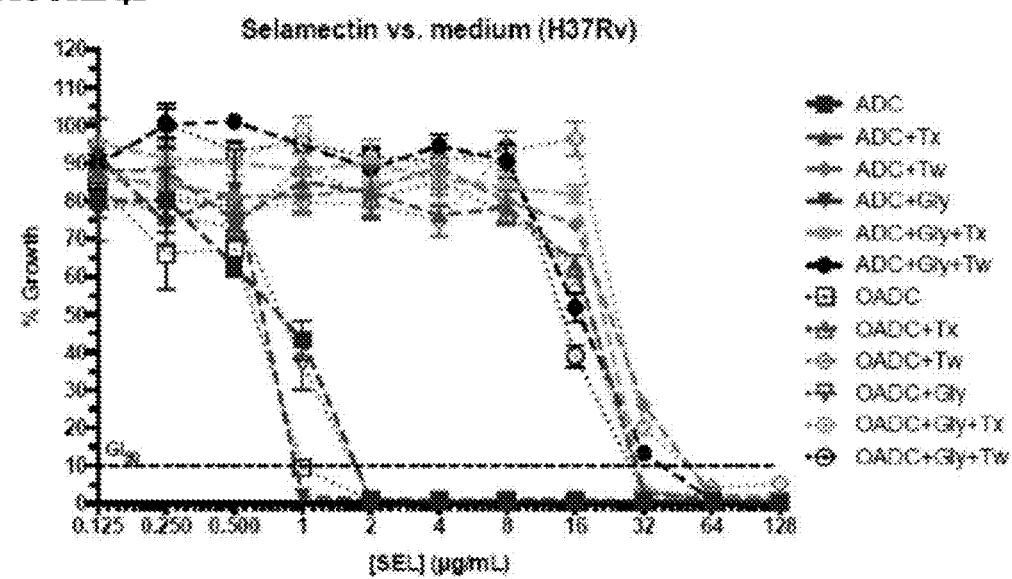
Figure 4B:
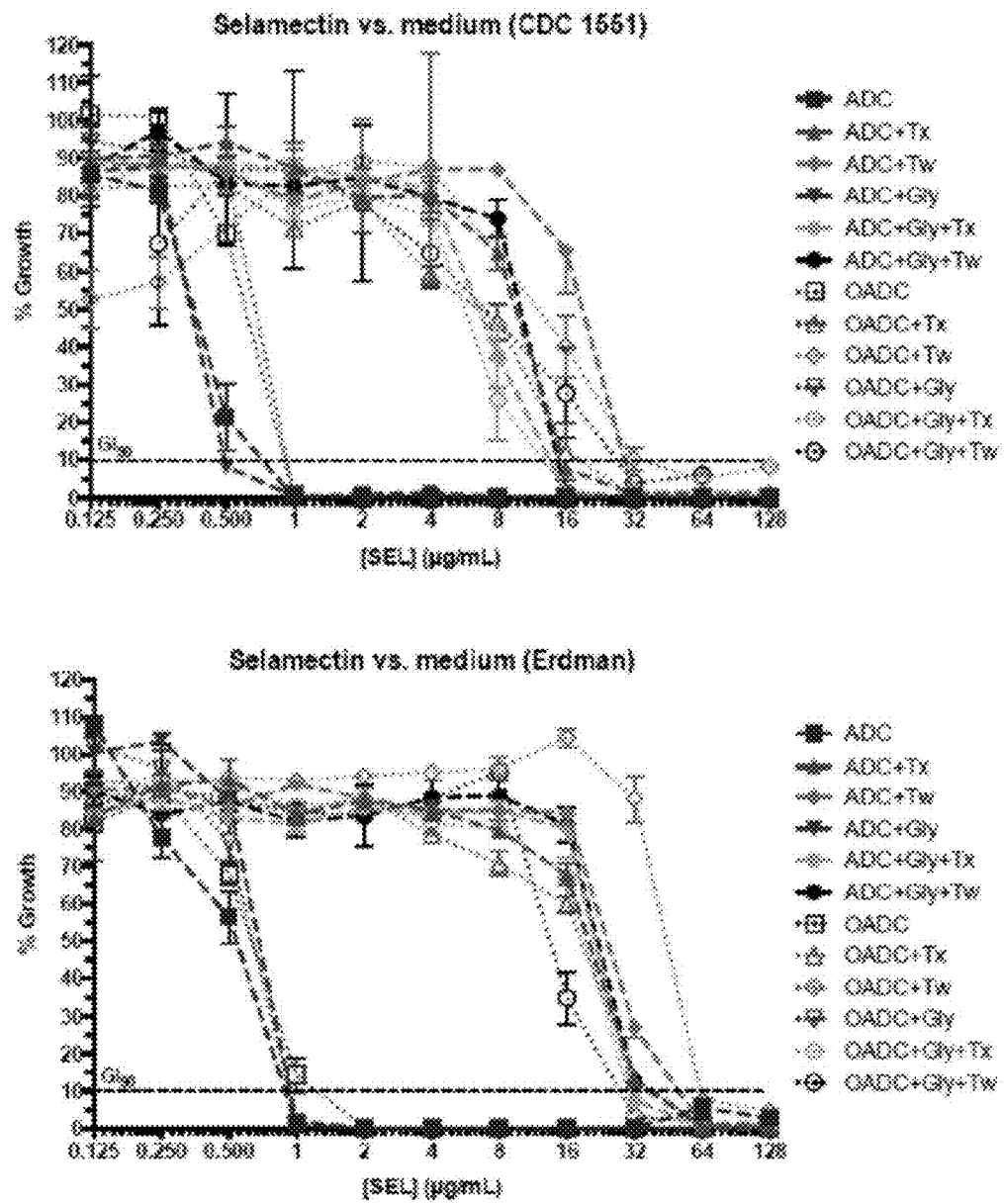
Figure 5:
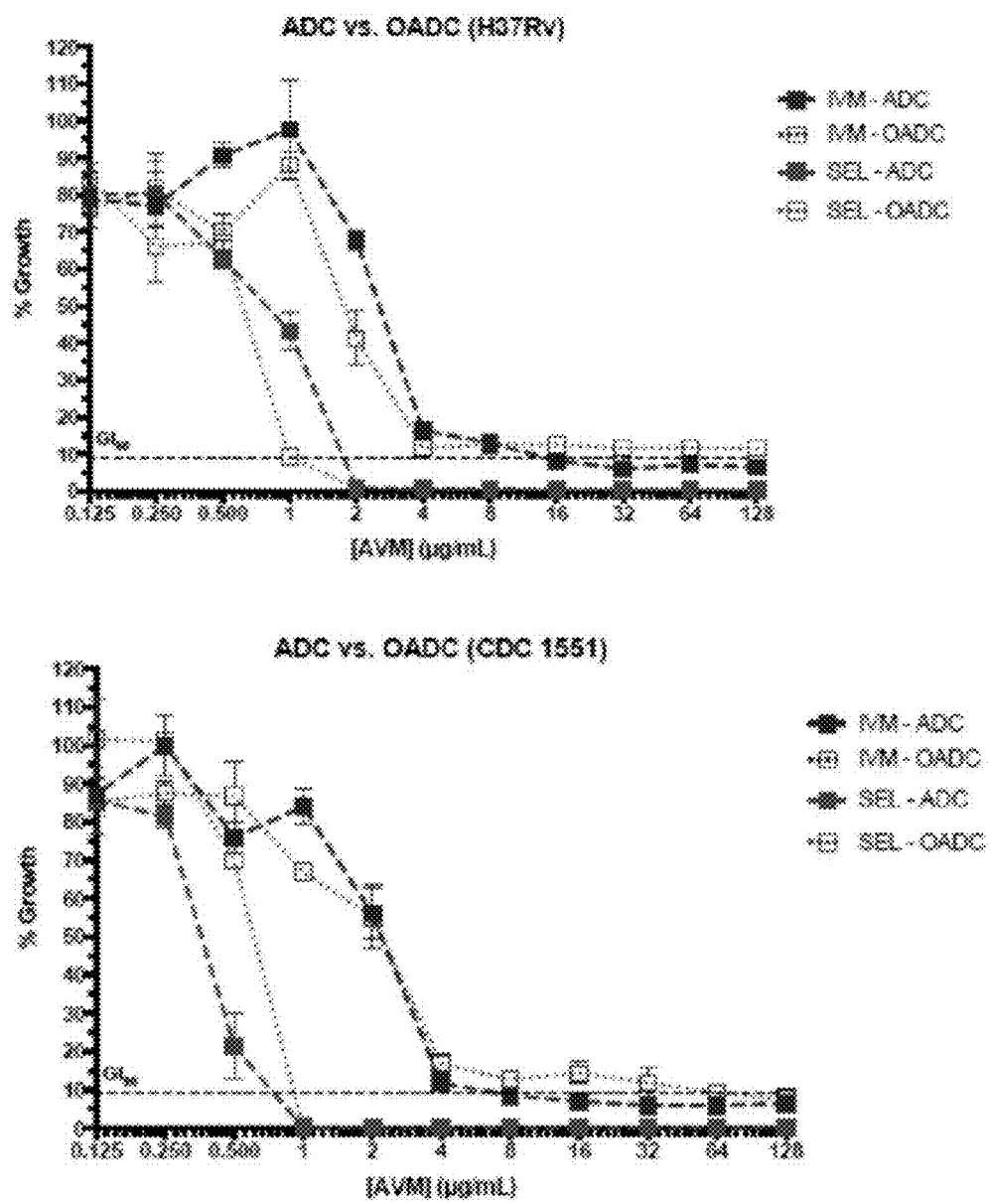
FIG. 5 shows the effect of oleic acid on the anti-*tuberculosis* activity of ivermectin and selamectin against *M. tuberculosis* strains H37Rv; CDC 1551; and Erdman 107.
Figure 5:
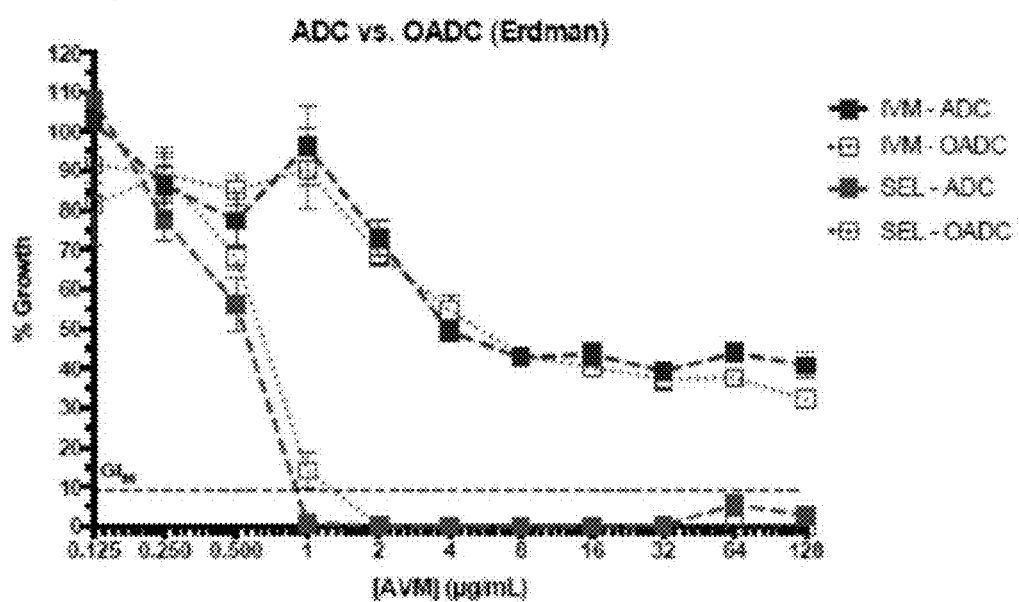
Figure 6:
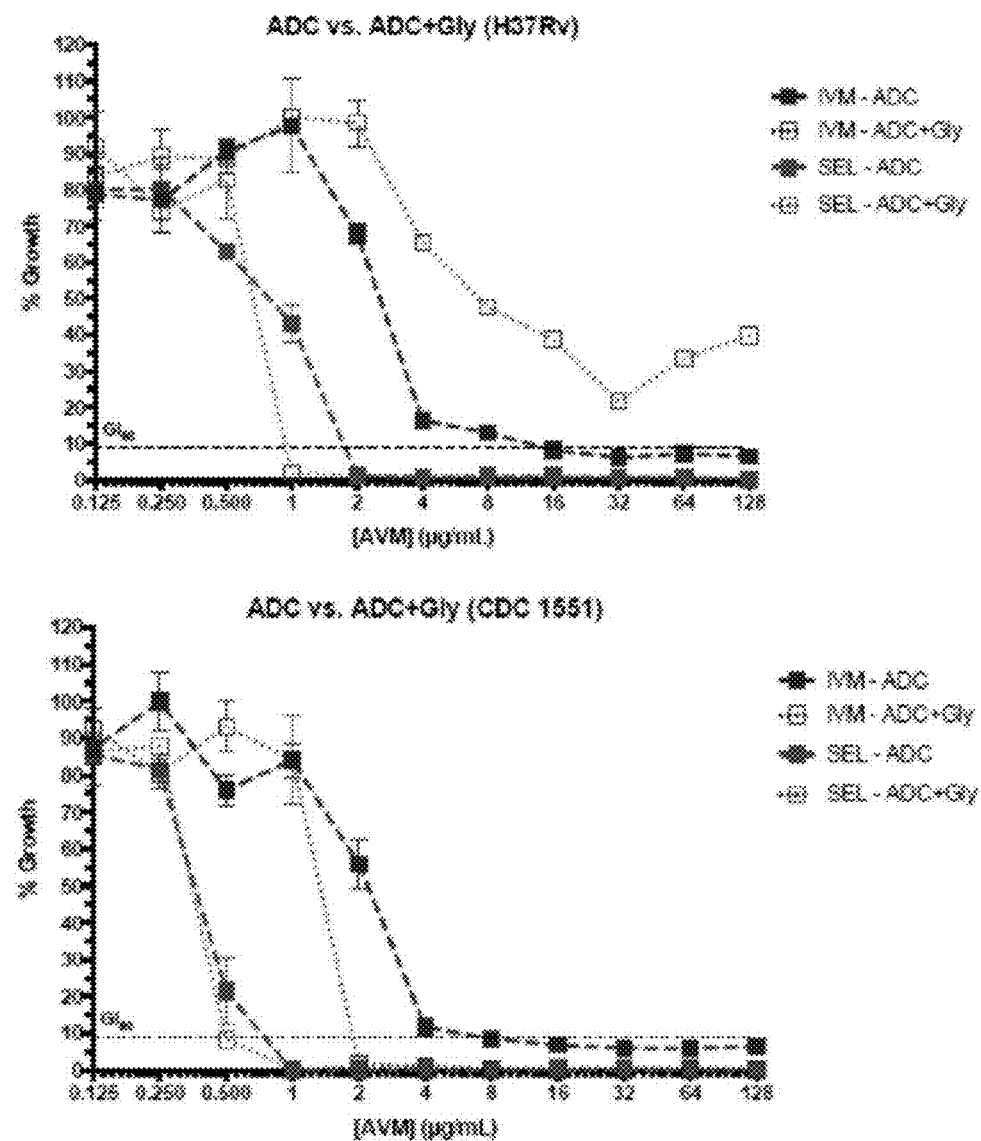
FIG. 6 shows the effect of glycerol on the anti-*tuberculosis* activity of ivermectin and selamectin against *M. tuberculosis* strains H37Rv; CDC 1551; and Erdman 107.
Figure 6:
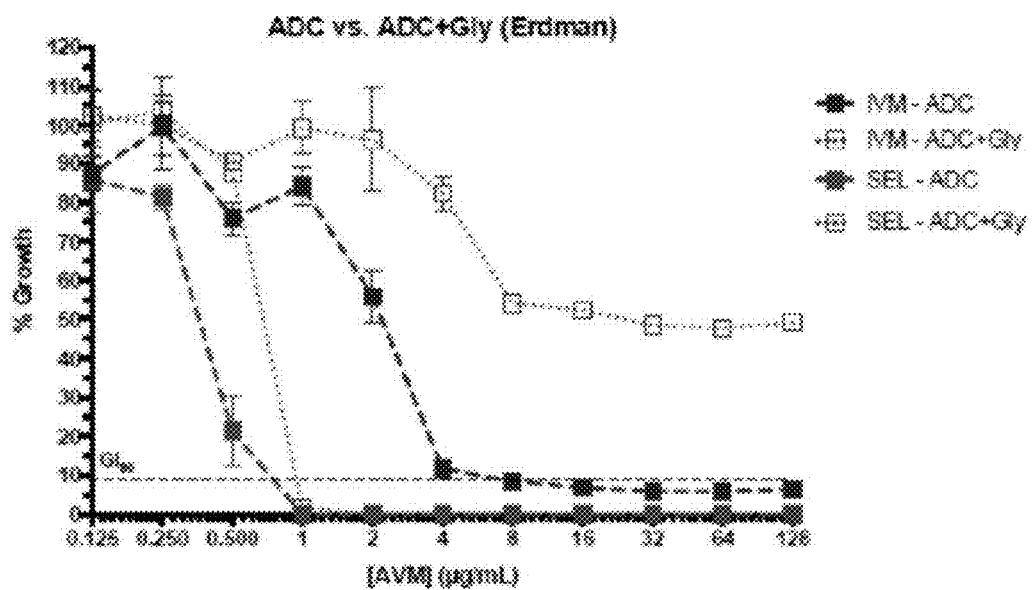
Figure 7A:
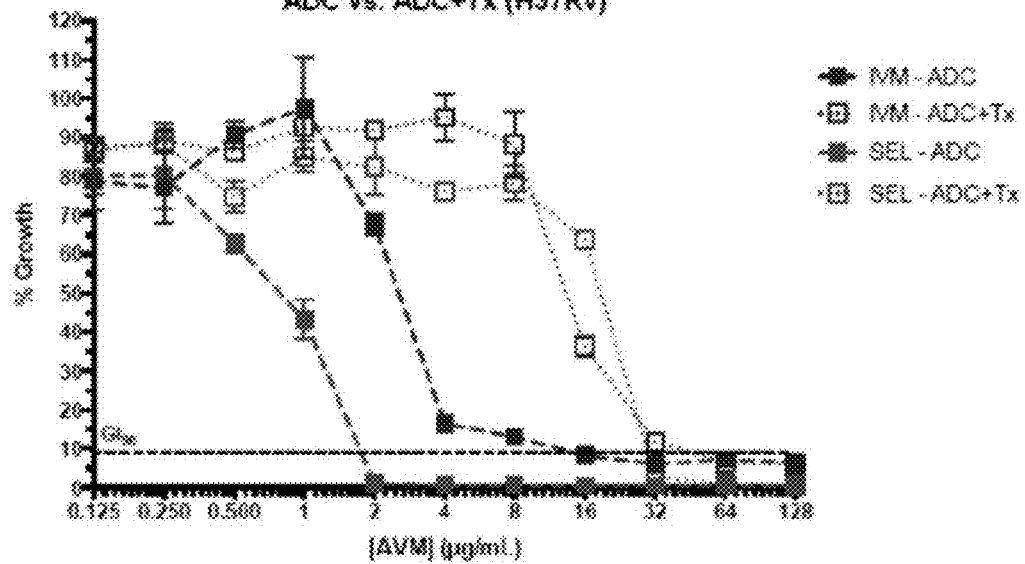
FIGS. 7A and 7B show effects of (FIG. 7A) tyloxapol and (FIG. 7B) Tween 80 on the anti-*tuberculosis* activity of ivermectin and selamectin against *M. tuberculosis* strains H37Rv; CDC 1551; and Erdman 107.
Figure 7A:
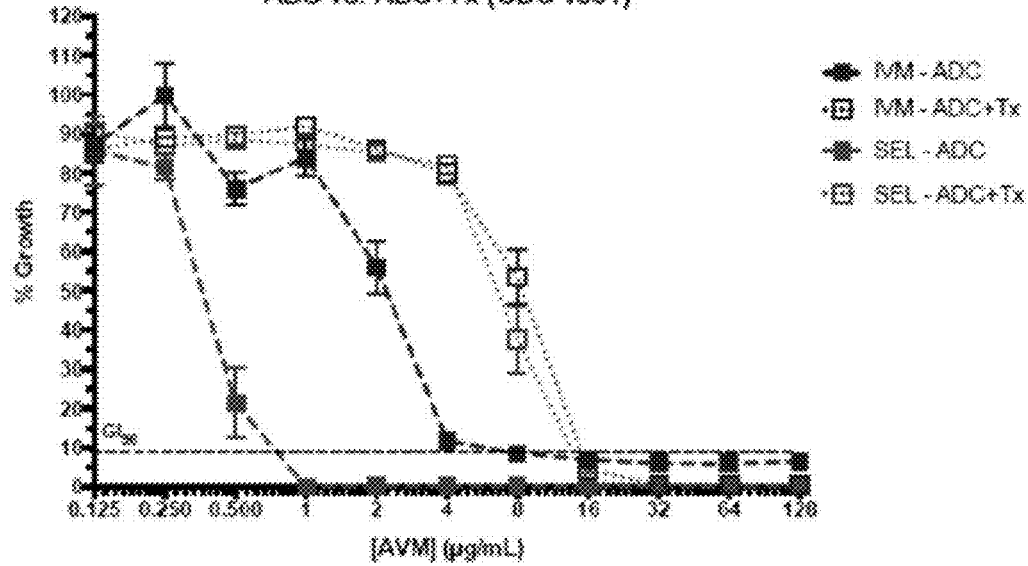
Figure 7A:
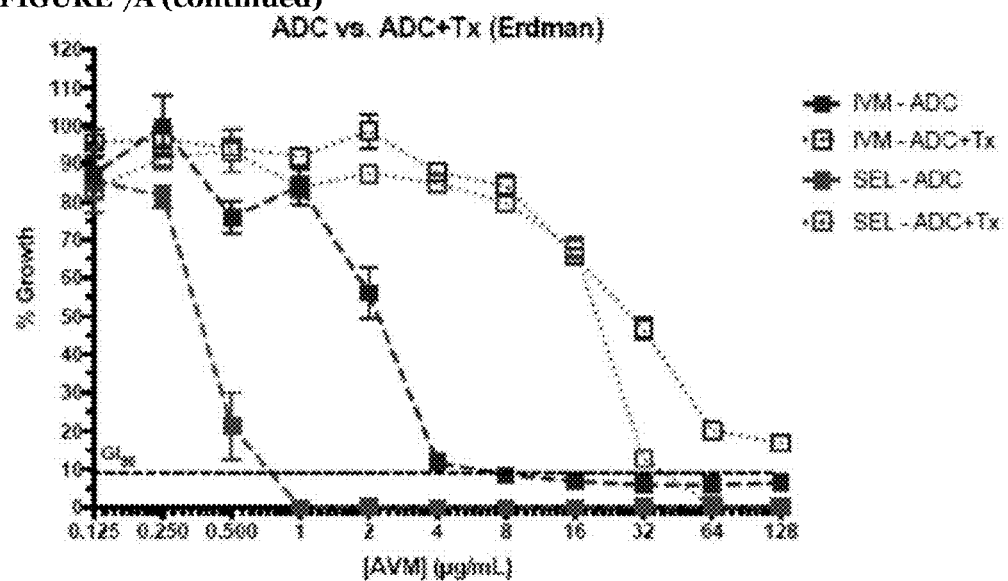
Figure 7B:
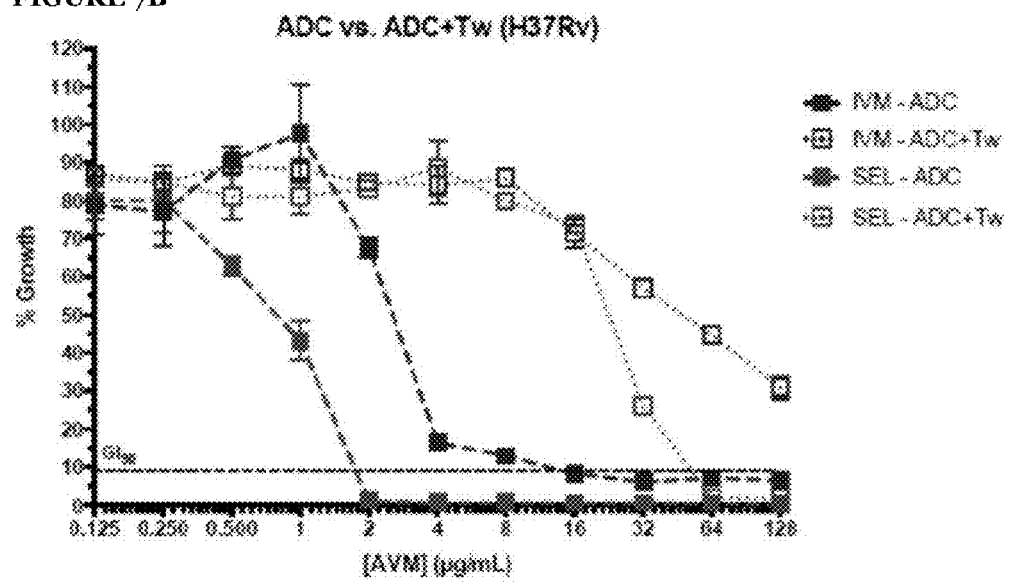
Figure 7B:
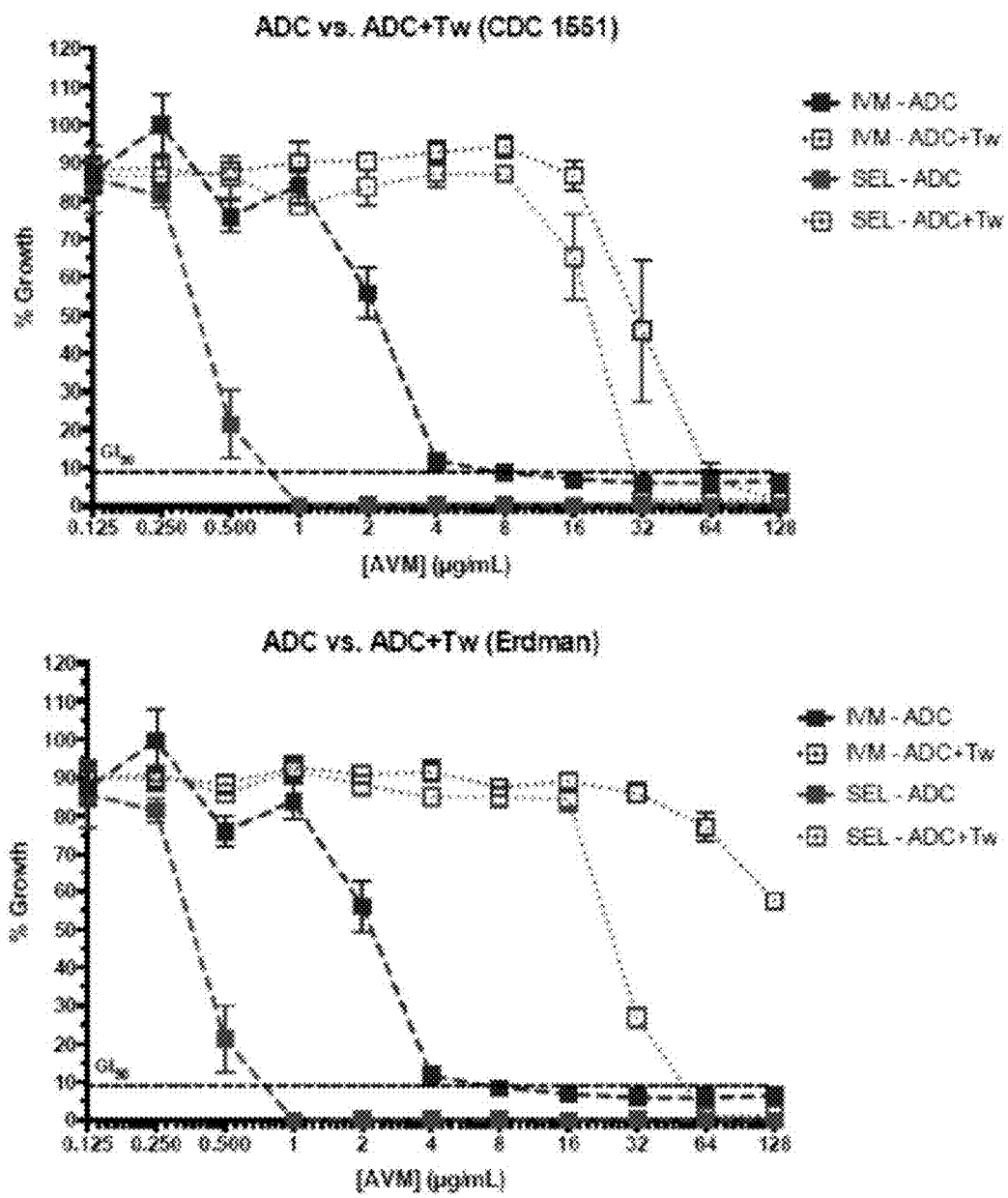
Figure 8:
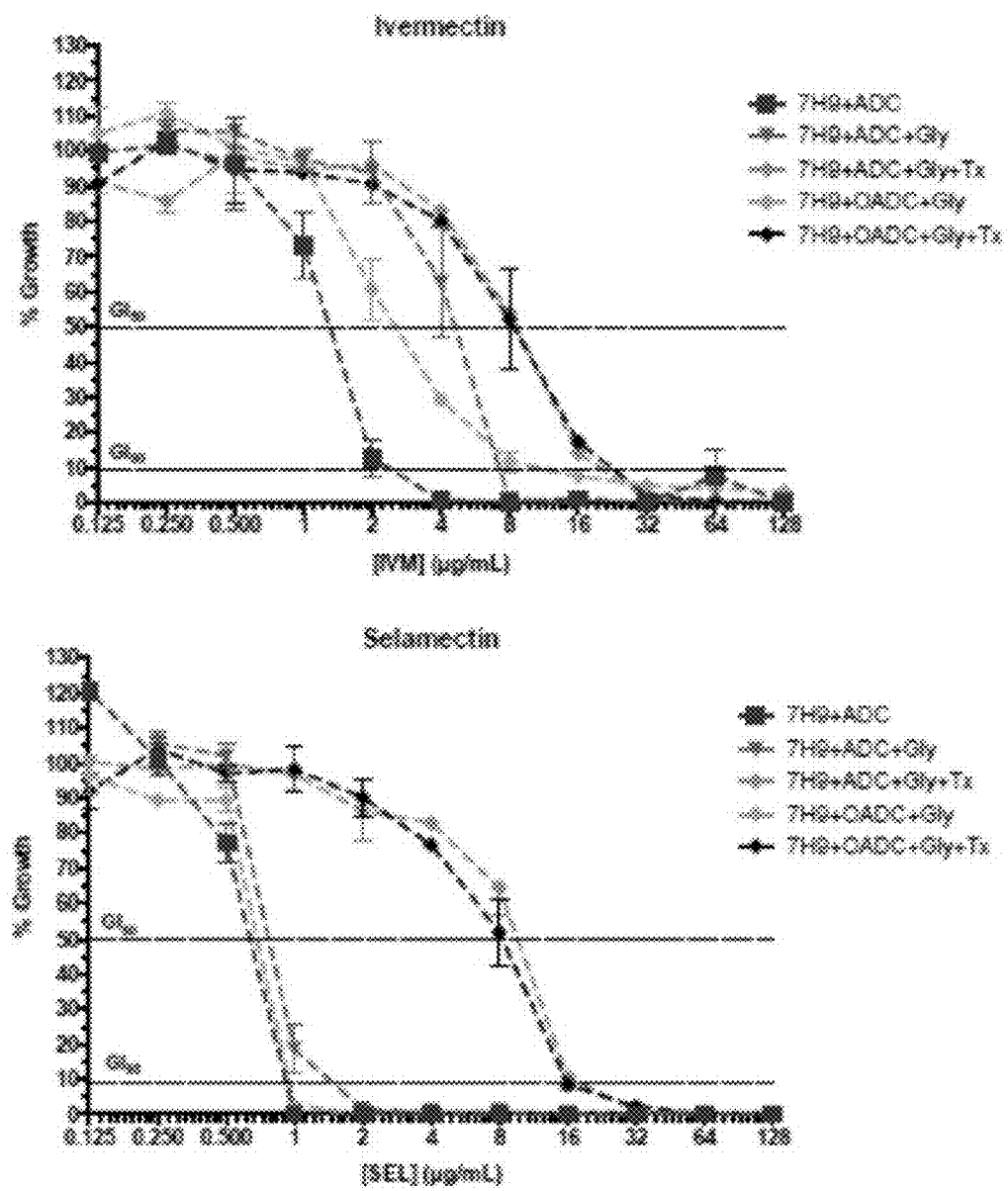
FIG. 8 shows a comparison of dose-response curves for ivermectin, selamectin, doramectin and moxidectin in different media against *M. tuberculosis* strain H37Rv.
Figure 8:
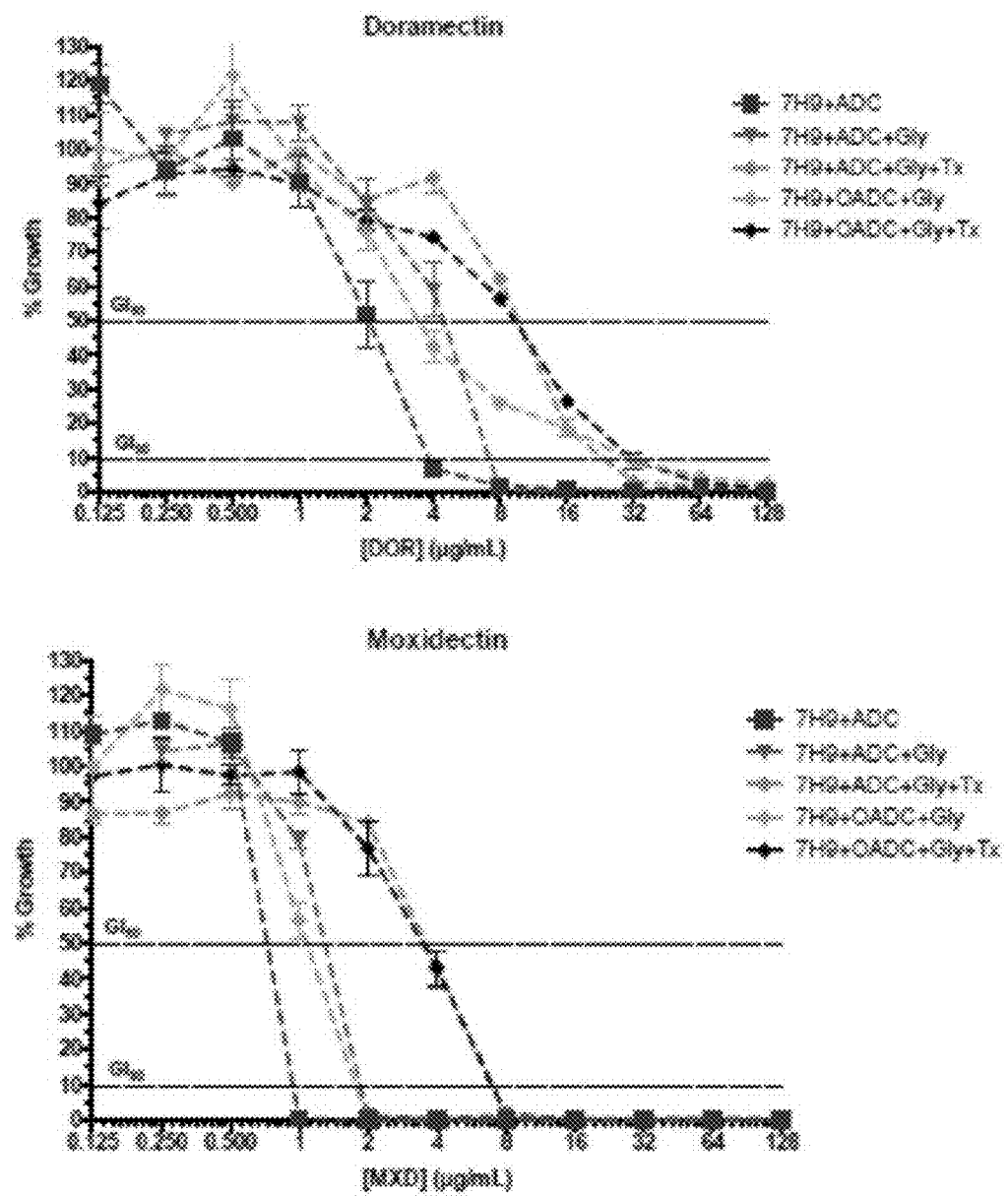

To address the question of whether avermectins and milbemycins are bactericidal or bacteriostatic, survival kinetic experiments were done for ivermectin, selamectin, and moxidectin (see FIG. 2). Two experiments performed independently, under similar but not identical growth conditions, measured kill kinetics. In the first experiment (FIG. 2, Panel A), 21-day kill curves were performed using various concentrations of ivermectin, selamectin, and moxidectin against the laboratory *M. tuberculosis* strain H37Rv. Here, selamectin showed the strongest bactericidal profile. All avermectins proved to be bactericidal, reducing initial bacterial viability up to 6 orders of magnitude (the limits of CFU detection). In the comparable kill kinetic experiment performed independently (FIG. 2, Panel B) the activity of the same dose (20 μg/ml) of each of the avermectins was measured over the same time period against *M. tuberculosis* H37Rv and mc25857 (an MDR strain; see Table 2 for details). Results were consistent with those described above. Moreover, all compounds tested showed promising bactericidal activity against the MDR strain, which was consistent with the MIC data and suggests the potential for avermectins and milbemycins in the treatment of MDR and XDR TB patients.

Example 3

In Vitro Pharmacodynamics Showed Concentration and Exposure-Dependent Bactericidal Activities of Avermectins and Milbemycins Against *M. tuberculosis*

The in vitro pharmacodynamic parameters of the avermectins and milbemycins were further analyzed in a third experiment (FIG. 3). In vitro dose-response curves for IVM, MDX, and SEL were obtained by plotting the change in log 10 CFU of the inoculum against the drug concentration C/MIC. Using an alternative method to visualize kill kinetics, each compound concentration was multiplied by the time of exposure (C×T in days) and then divided by the MIC to give the in vitro area under the concentration-time curve (AUC/MIC ratio), a standard measure of drug exposure. These analyses both showed that the tested compounds had exposure-dependent kill kinetics against *M. tuberculosis* under standard in vitro broth conditions. The AUC/MIC needed to achieve 1 log 10 CFU/ml reduction varied between 2 and 4, while a bactericidal effect (4 log 10 CFU/ml reduction, 99.99% killing) required AUC/MIC ratios between 12 and 14. From a TB drug treatment perspective, this value indicates the strong bactericidal effect of avermectins and milbemycins relative to rifampin, the standard frontline drug. The AUC at 24 h (AUC24)/MIC value required for a comparable 1 log 10 CFU/ml reduction of the first-line anti*tuberculosis* drug rifampin is more than 10 times higher (Jayaram R, et al. 2003. Pharmacokinetics-pharmacodynamics of rifampin in an aerosol infection model of *tuberculosis*. Antimicrob. Agents Chemother. 47: 2118-2124).

Example 4

Comparison of Anti-*Tuberculosis* Activity of Compounds Under Different Media Conditions The study of growth in different media may be important for the establishment of clinical guidelines for testing avermectins or milbemycins. In FIGS. 4A and 4B the anti-*tuberculosis* activity of ivermectin and selamectin, respectively compared under different media conditions against *M. tuberculosis* strains H37Rv; CDC 1551; and Erdman 107. Similarly, in FIGS. 5 and 6 the effects of oleic acid and glycerol, respectively are compared on the anti-*tuberculosis* activity of ivermectin and selamectin against *M. tuberculosis* strains H37Rv; CDC 1551; and Erdman 107. In FIGS. 7A and 7B the effects of tyloxapol and Tween 80 on the anti-*tuberculosis* activity of ivermectin and selamectin against *M. tuberculosis* strains H37Rv; CDC 1551; and Erdman 107 are compared.

Lastly, FIG. 8 shows a comparison of dose-response curves for ivermectin, selamectin, doramectin and moxidectin under different media against *M. tuberculosis* strain H37Rv.

Example 5

Avermectins Kill *M. tuberculosis*, Including MDR Strains

Figure 9:
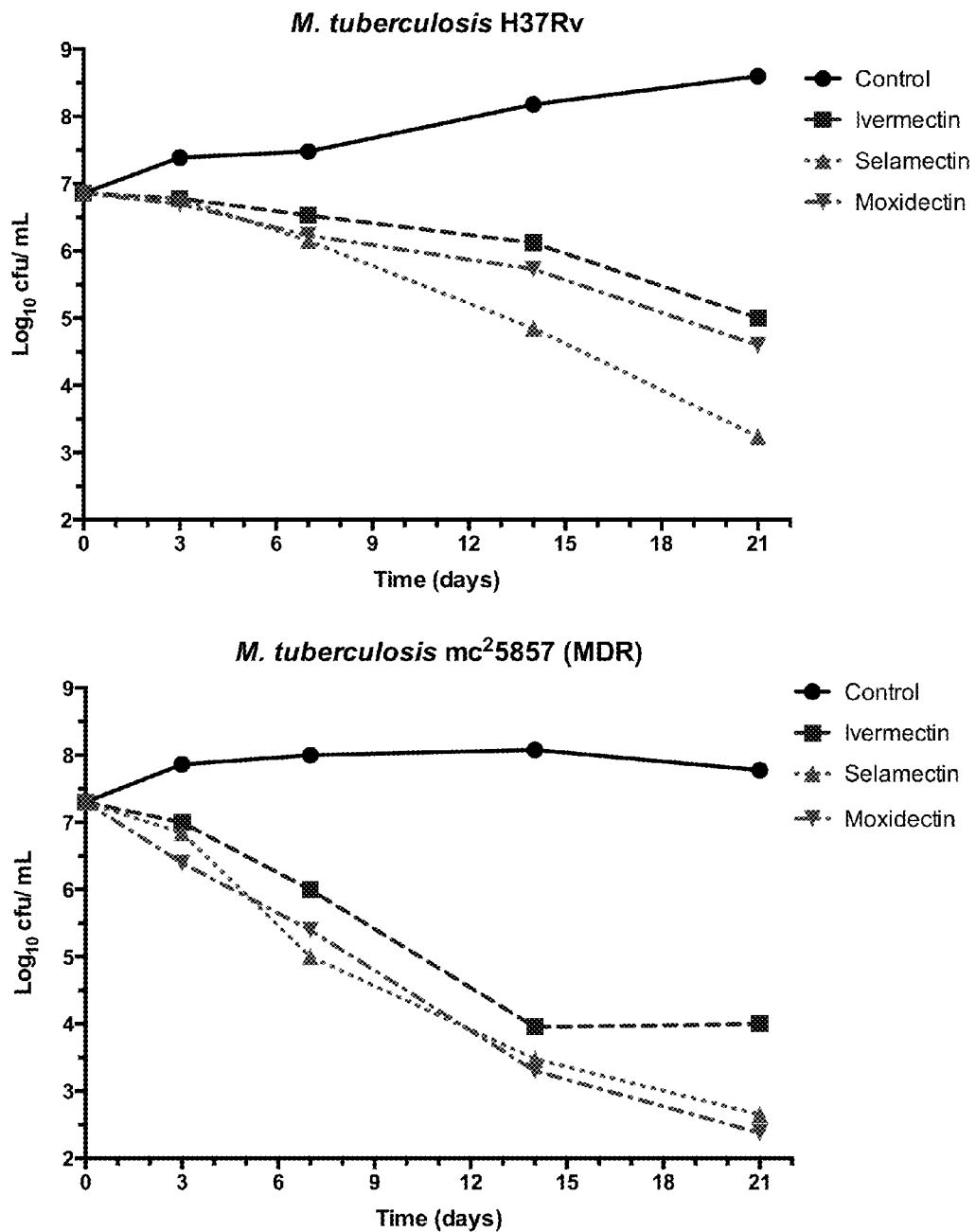
FIG. 9 shows a plot of time kill kinetics for ivermectin, selamectin, and moxidectin against *M. tuberculosis* H37Rv and mc$^2$ 5857 (MDR) strains.
Figure 10:
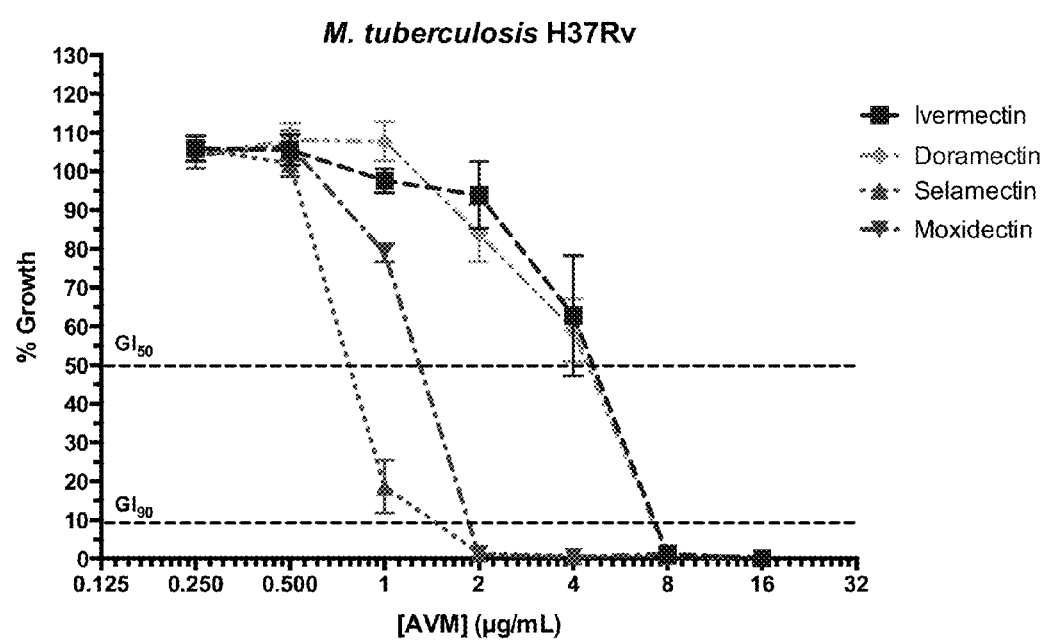
FIG. 10 shows dose response curves for selamectin and moxidectin have increased activity, compared to ivermectin and doramectin, against *M. tuberculosis* H37Rv, and against MDR clinical isolates.
Figure 11:
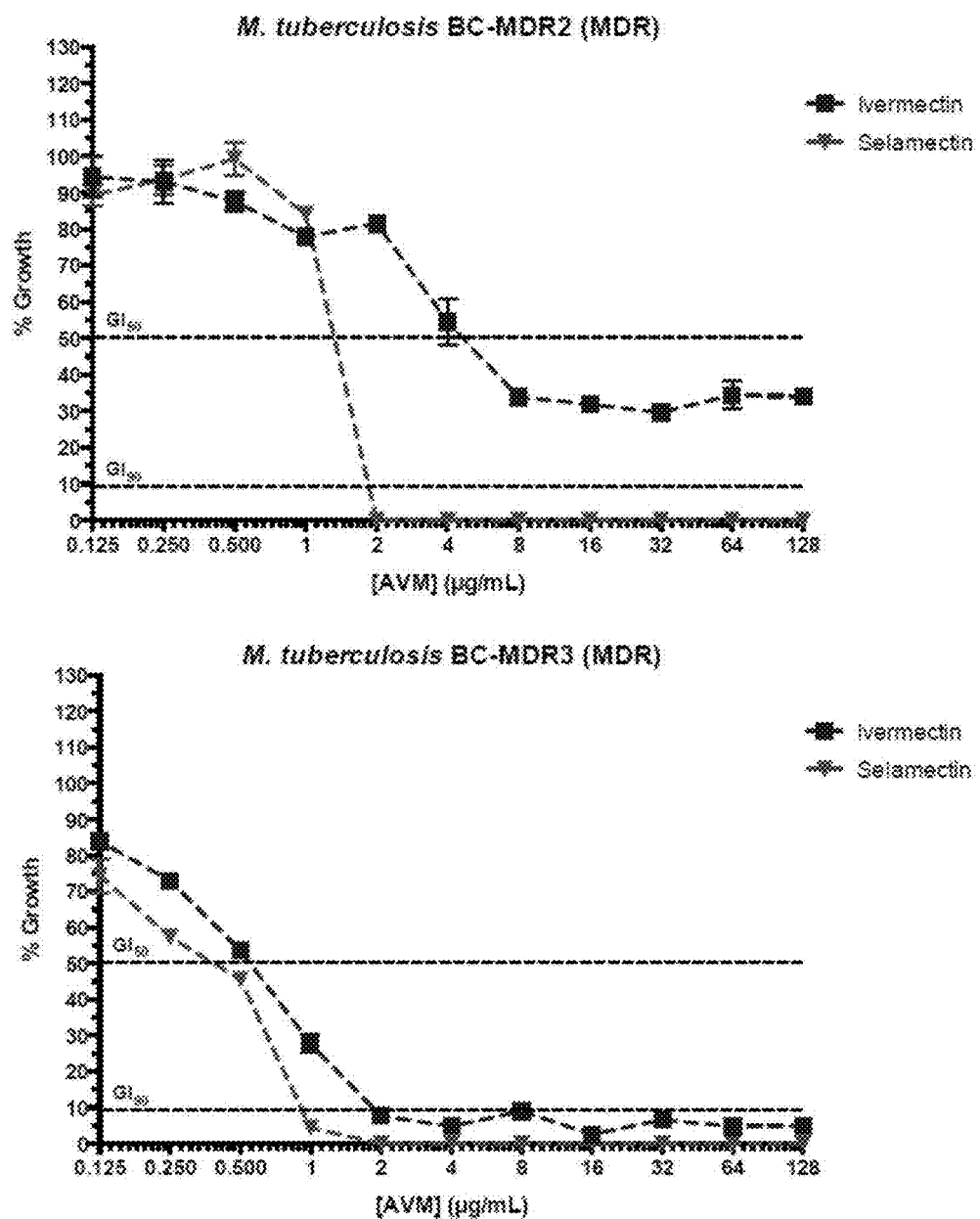
FIG. 11 shows dose response curves for selamectin and ivermectin against *M. tuberculosis* MDR clinical isolates BC-MDR2, BC-MDR3, BC-MDR4 and BC-MDR5.
Figure 11:
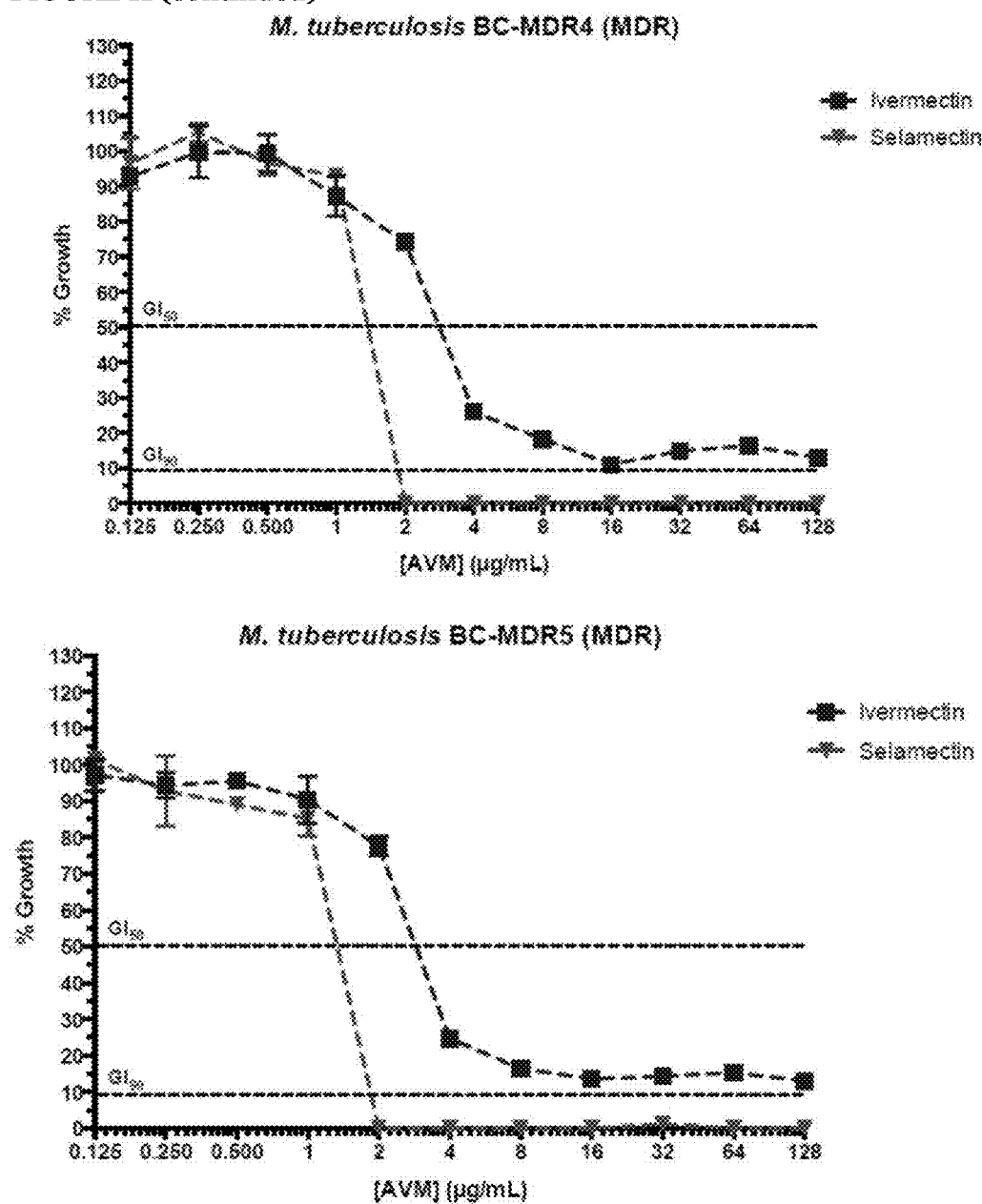
Figure 12B:
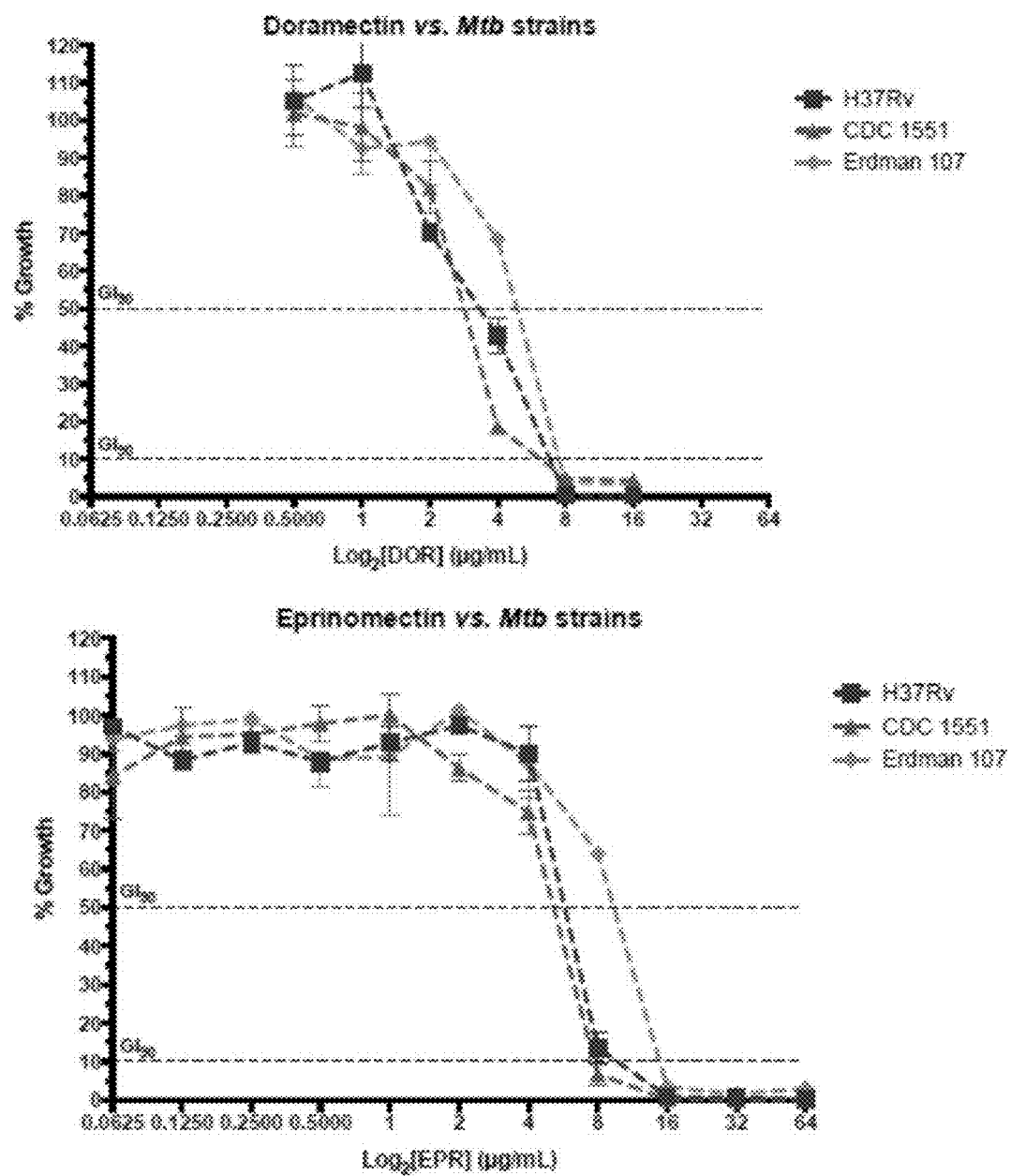
Figure 12D:
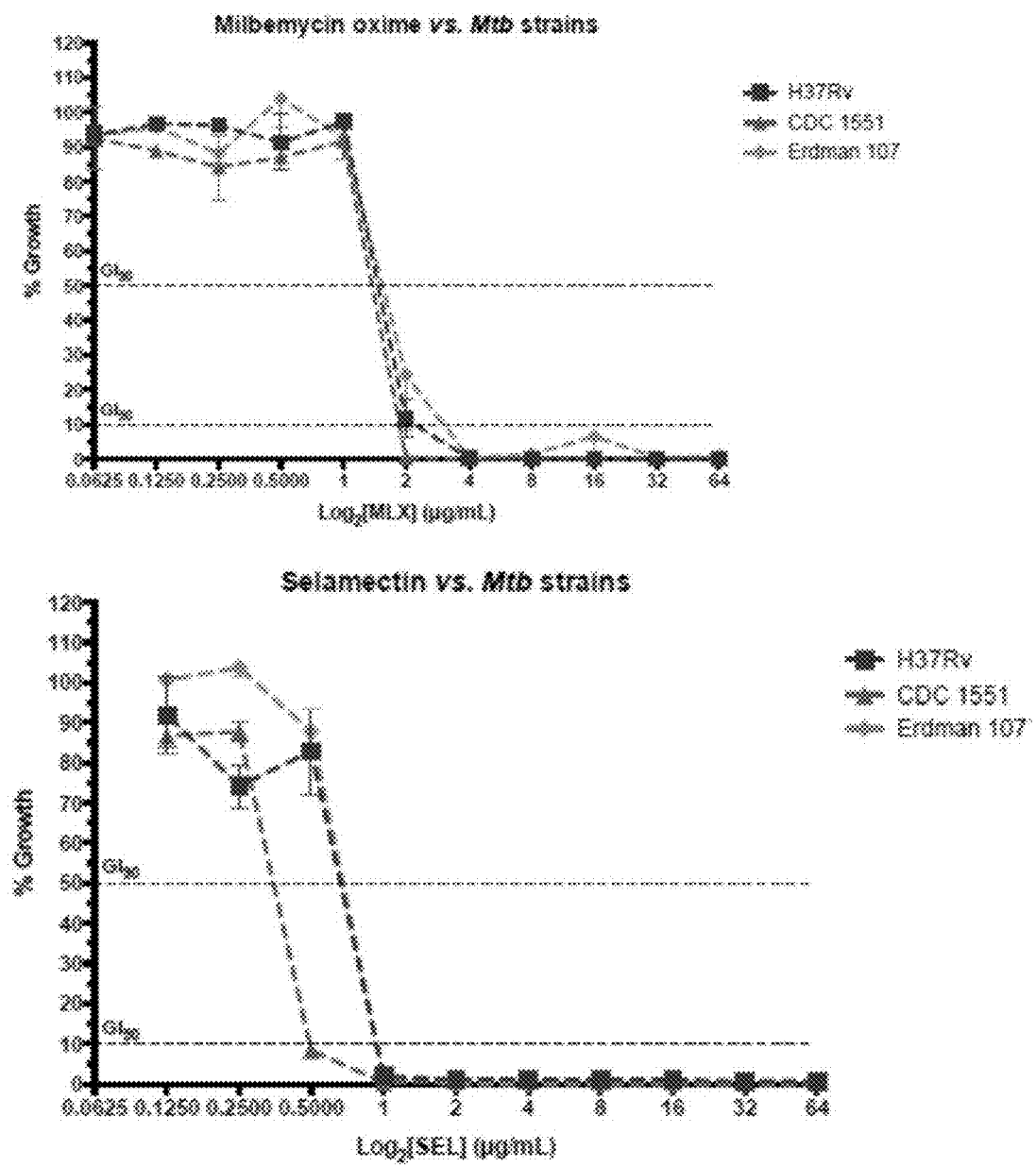

As shown in FIG. 9 time kill kinetics for ivermectin, selamectin, and moxidectin against *M. tuberculosis* H37Rv and $mc^2$ 5857 (MDR) strains are compared. Similarly, in FIG. 10 dose response curves for selamectin and moxidectin show increased activity, compared to ivermectin and doramectin, against *M. tuberculosis* H37Rv, and against an MDR clinical isolate. Lastly, FIG. 11 shows dose response curves for selamectin and ivermectin against four *M. tuberculosis* MDR clinical isolates BC-MDR2, BC-MDR3, BC-MDR4 and BC-MDR5, where selamectin is consistently more active than ivermectin.

Example 6

Pharmacokinetic Analyses and In Vivo Assays Suggest that Selamectin has Particular Promise for TB Drug Treatment when Compared to Ivermectin and Moxidectin As shown below in TABLE 4, AUC/MIC values of >15 for selamectin, which is a strong predictor of in vivo activity.

TABLE 4

| Drug | Species | Dose (oral unless indicated) | Cmax (ng/mL) | T½ (days) | AUC (ng * h/mL) | Theoretical AUC/MIC | References (PubMed ID#) |
|---|---|---|---|---|---|---|---|
| Ivermectin | Humans | 12 mg (165 µg/kg) | 47 | nd | nd | nd | PMID: 12362927 |
| | | 30 mg (347-541 µg/kg) | 85 | 19 h | 2819 | 0.47 | PMID: 18446504 |
| | | 30 mg (fed) | 260 | 15 h | 4564 | 0.76 | |
| | | 90 mg (1031-1466 µg/kg) | 158 | 19 h | 2910 | 0.49 | |
| | | 120 mg (1404-2000 µg/kg) | 247 | 19 h | 4547 | 0.76 | |
| | Dogs | 250 µg/kg | 132 | 80 h | 5600 | 0.93 | PMID: 1496814 |
| | Horses | 200 µg/kg | 44 | 20 h | 3184 | 0.53 | PMID: 12093191 |
| | Mouse (plasma) | 0.2 mg/kg | 20 | 9.3 h | 573 | 0.10 | PMID: 19161460 |
| | Mouse (lung) | 0.2 mg/kg | 20 | nd | nd | nd | |
| Moxidectin | Humans | 3 mg fast | 22.4 | 33.8 | 1442 | 0.48 | PMID: 14517193 |
| | | 9 mg fast | 57.9 | 34.6 | 3024 | 1.01 | |
| | | 18 mg fast | 141 | 22 | 5856 | 1.95 | |
| | | 36 mg fast | 289 | 20.2 | 10824 | 3.61 | |
| | | 36 mg fed | 296 | 25.7 | 14976 | 4.99 | |
| | Dogs | 250 µg/kg | 234 | 621 h | 11800 | 3.93 | ProHeart 6 (moxidectin) - Product profile |
| Selamectin | Dogs males | 6 mg/kg (topical) | 12.72 | 12.14 | 4609 | 1.54 | Stronghold (selamenctin) - Product profile |
| | Dogs female | 6 mg/kg (topical) | 22.65 | 10.73 | 8903 | 2.97 | |
| | Mouse (plasma) | 12 mg/kg | 3714 | 5.5 | 62285.7 | 20.76 | PMID: 19161460 |
| | Mouse (lung) | 12 mg/kg | 7500 | nd | nd | nd | |
| | Rats | 10 mg/kg | >1000 | 10.3 h | nd | nd | Stronghold (selamenctin) - Product profile |
| | Dogs | 24 mg/kg | 7630 | 45.7 h | 227901 | 75.97 | PMID: 12213114 |
| | | 24 mg/kg (topical) | 86.5 | 266 | 15229 | 5.08 | |
| | Cats | 24 mg/kg | 11929 | 97.7 | 1109933 | 369.98 | PMID: 12213114 |
| | | 24 mg/kg (topical) | 5513 | 198 | 743349 | 247.78 | |

Theoretical AUC/MIC values were calculated based on in vitro MIC values of the avermectins against the *M. tuberculosis* H37Rv strain. MIC values (in ng/mL): ivermectin, 6,000; selamectin: 3,000; and moxidectin: 3,000.

Using an acute TB model, immune compromised mice were low-dose aerosol infected and then left untreated for 13 days to allow the infection to become established before 9 days of consecutive drug therapy was initiated. Drugs were administered orally and $Log_{10}$ cfu reductions in the lungs were compared to and untreated group (vehicle) to rifampin treatment. In this assay selamectin showed activity at both a 10 mg/kg and 50 mg/kg dose (p value 0.046 and 0.015, respectively) in vivo against *Mycobacterium tuberculosis* (H37Rv), whereas ivermectin against Erdman 107, did not show activity in this assay at both 5 and 10 mg/kg doses. The lack of activity in the in vivo assay suggests that an alternative dosing, formulation and/or mode of delivery may be utilized to obtain significant activity for ivermectin and other compounds. Rifampicin was included as control.

TABLE 5

| Drug | Mouse model | Mtb strain | Dose (mg/kg bw) | Route | Formulation | Log10 cfu reduction (lungs) | Toxicity | p < 0.05 |
|---|---|---|---|---|---|---|---|---|
| Ivermectin | Acute (GKO) | Erdman | 5 | PO | 50/35/15 H2O/PEG300/PG | 0.32 | None | No |
| Ivermectin | Acute (GKO) | Erdman | 10 | PO | 50/35/15 H2O/PEG300/PG | 0.4 | None | No |
| Ivermectin | Chronic (Balb/C) | Erdman | 10 | PO | 50/35/15 H2O/PEG300/PG | −0.11 | None | No |
| Selamectin | Acute (SCID) | H37Rv | 10 | PO | Sesame oil | −0.42 | None | 0.046 |
| Selamectin | Acute (SCID) | H37Rv | 50 | PO | Sesame oil | −0.62 | None | 0.015 |
| Selamectin | Acute (SCID) | H37Rv | 100 | PO | Sesame oil | −0.23 | Low | No |
| Selamectin | Acute (SCID) | H37Rv | 200 | PO | Sesame oil | −0.23 | Low/moderate | No |
| Rifampin | Acute (SCID) | H37Rv | 1 | PO | 5% DMSO | −0.08 | None | No |
| Rifampin | Acute (SCID) | H37Rv | 10 | PO | 5% DMSO | −1.17 | None | <0.0001 |

Example 7

Dose Response Abamectin, Emamectin, Doramectin, Eprinomectin, Ivermectin, Moxidectin, Milbemycin Oxime and Selamectin Against *M. tuberculosis* Strains H37Rv, CDC 1551, and Erdman 107

As shown in FIGS. 12A-12D, all of the tested compounds showed varying degrees of activity against the tested *M. tuberculosis* strains. However, selamectin of all the tested compounds shows the best activity on the *M. tuberculosis* strains H37Rv, CDC 1551, and Erdman 107. This data also correlate with data obtained against MDR- and XDR-TB strains (Lim et al. (2013) Anthelmintic Avermectins Kill *Mycobacterium tuberculosis*, Including Multidrug-Resistant Clinical Strains. Antimicrob. Agents Chemother. Vol. 57. p. 1040-1046).

Example 8

Comparison of Antimicrobial Activities of Abamectin, Ivermectin, Moxidectin, and Selamectin Against Various Mycobacterial Species As shown below in TABLE 6 selamectin is generally the most effective against a variety of mycobacterial species.

TABLE 6

Antimicrobial activities of abamectin, ivermectin, moxidectin, and selamectin against different mycobacterial species.

| Mycobacterial species | | MIC (µg/mL) | | | |
|---|---|---|---|---|---|
| | | Abamectin | Ivermectin | Moxidectin | Selamectin |
| M. aurum | | 8 | 2 | 1 | 1 |
| M. avium | 702 | >256 | >256 | >256 | 64 |
| | 715 | >256 | >256 | >256 | 128 |
| | ATCC 25291 | ND | >128 | >128 | 16 |
| M. chelonae | | 16 | 4 | 4 | 2 |
| M. gordonae | 324 | 16 | 4 | 4 | <0.25 |
| M. intracellulare | 1403 ATCC35761 | 16 | 4 | 16 | 1 |
| | 1403 Trudeau | 16 | 4 | 32 | 1 |
| | D673 | 32 | 8 | >256 | 2 |
| | FM | 16 | 8 | >256 | 2 |
| M. microti | Ov254 | 256 | >256 | 4 | 2 |
| | 1601 | 16 | 4 | 4 | 1 |
| | 1608 | 64 | 256 | 4 | 2 |
| M. phlei | | >256 | 32 | 8 | 4 |

An important NTM pathogen is *M. abscessus*, *M. abscessus* is very closely related to *M. chelonea*, which is sometimes called a subspecies of *M. chelonea*. In fact, these two *Mycobacteria* are together sometimes called the "*M. abscessus/M. chelonea* complex". TABLE 6 shows that *M. chelonae* is avermectin sensitive.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

The invention claimed is:

1. A method of treating a subject having a mycobacterial infection, the method comprising:
   administering a pharmaceutically effective amount of at least one avermectin compound or at least one milbemycin compound, to a subject having a mycobacterial infection.

2. The method of claim 1, wherein at least one avermectin or milbemycin compound is selected from one or more of the following: abamectin; emamectin; eprinomectin; doramectin; ivermectin; selamectin; milbemectin; milbemycin oxime; moxidectin; and nemadectin.

3. The method of claim 1, wherein the at least one avermectin or milbemycin compound is selected from abamectin, emamectin, eprinomectin, doramectin, ivermectin, milbemycin oxime, moxidectin or selamectin.

4. The method of claim 1, wherein the at least one avermectin or milbemycin compound is selamectin.

5. The method of claim 1, wherein the at least one avermectin or milbemycin compound is moxidectin.

6. The method of claim 1, wherein the at least one avermectin or milbemycin compound is ivermectin.

7. The method of claim 1, wherein the mycobacterial infection is *tuberculosis*.

8. The method of claim 1, wherein the mycobacterial infection is a *M. avium intracellulare*, *M. avium*, *M. kansasii*, *M. fortuitum*, *M. abscessus*, or *M. marinum* infection.

9. The method of claim 1, wherein an organism responsible for the mycobacterial infection is *M. tuberculosis*.

10. The method of claim 9, wherein an organism responsible for the mycobacterial infection is MDR-*M. tuberculosis*, XDR-*M. tuberculosis*, or TDR-*M. tuberculosis*.

11. The method of claim 10, wherein the subject has latent *tuberculosis* disease.

12. The method of claim 1, wherein an organism responsible for the mycobacterial infection is a *mycobacterium* of the *tuberculosis* complex.

13. The method of claim 12, wherein the organism responsible for the mycobacterial infection is *M. tuberculosis*, or *M. africanum*, or *M. bovis* and the *Bacillus* Calmette-Guérin strain, or *M. microti*, or *M. canettii*, or *M. caprae*, or *M. pinnipedii*.

14. The method of claim 1, wherein an organism responsible for the mycobacterial infection is a non-tuberculous *mycobacteria* (NTM).

15. The method of claim 1, wherein an organism responsible for the mycobacterial infection is selected from one or more of the following: *M. avium*; *M. smegmatis*; *M. abscessus*; *M. africanum*; *M. canetti*; *M. microti*; *M. ulcerans*; *M. avium intracellulare*; *M. kansasii*; *M. fortuitum*; *M. marinum*; *M. chelonae*; and *M. leprae*.

16. The method of claim 1, wherein the subject is a mammal.

17. The method of claim 1, wherein the subject is a human, rat, mouse, dog, cat, cow, sheep, horse or pig.

18. The method of claim 17, wherein the subject is a cow.

19. The method of claim 18, wherein the organism responsible for the mycobacterial infection is *Mycobacterium avium* subsp. *paratuberculosis*.

20. The method of claim 18, wherein the mycobacterial infection causes Johne's disease.

21. The method of claim 1, wherein the subject has active *tuberculosis* disease.

* * * * *